US012611368B2

(12) United States Patent
Orlando et al.

(10) Patent No.: US 12,611,368 B2
(45) Date of Patent: Apr. 28, 2026

(54) DRY COMPOSITIONS AND/OR EMULSIONS FOR CHEMICAL AND PHYSICAL SUN PROTECTION AND USE THEREOF

(71) Applicant: Omya International AG, Oftringen (CH)

(72) Inventors: Fabrizio Orlando, Würenlos (CH); Jamal Ftouni, Zofingen (CH)

(73) Assignee: Omya International AG, Oftringen (CH)

( * ) Notice: Subject to any disclaimer, the term of this patent is extended or adjusted under 35 U.S.C. 154(b) by 523 days.

(21) Appl. No.: 17/996,794

(22) PCT Filed: May 3, 2021

(86) PCT No.: PCT/EP2021/061566
§ 371 (c)(1),
(2) Date: Oct. 21, 2022

(87) PCT Pub. No.: WO2021/224182
PCT Pub. Date: Nov. 11, 2021

(65) Prior Publication Data
US 2023/0181431 A1     Jun. 15, 2023

(30) Foreign Application Priority Data
May 4, 2020     (EP) ..................................... 20172715

(51) Int. Cl.
*A61Q 17/04*          (2006.01)
*A61K 8/06*           (2006.01)
*A61K 8/19*           (2006.01)
*A61K 8/81*           (2006.01)

(52) U.S. Cl.
CPC .................. *A61K 8/19* (2013.01); *A61K 8/06* (2013.01); *A61K 8/81* (2013.01); *A61Q 17/04* (2013.01)

(58) Field of Classification Search
None
See application file for complete search history.

(56) References Cited

U.S. PATENT DOCUMENTS

| | | | |
|---|---|---|---|
| 1,361,324 A | 12/1920 | Grunwald | |
| 5,979,461 A | 11/1999 | Bensalem et al. | |
| 9,354,180 B2 | 5/2016 | Jiang | |
| 2004/0020410 A1 | 2/2004 | Gane et al. | |
| 2006/0280702 A1 | 12/2006 | SenGupta et al. | |
| 2009/0186768 A1 | 7/2009 | Hoobler et al. | |
| 2010/0202985 A1* | 8/2010 | SenGupta ................ | A61K 8/27 424/59 |
| 2012/0052187 A1 | 3/2012 | May | |
| 2016/0037772 A1 | 2/2016 | Guerrero Mendez | |
| 2016/0312031 A1* | 10/2016 | Qiu .......................... | C08K 3/22 |
| 2017/0226344 A1 | 8/2017 | Berlin | |
| 2017/0333301 A1 | 11/2017 | Yamaki et al. | |

| | | | |
|---|---|---|---|
| 2019/0343736 A1 | 11/2019 | Qiu et al. | |
| 2019/0380927 A1* | 12/2019 | Budde ...................... | A61K 8/29 |
| 2023/0000072 A1 | 1/2023 | Ftouni et al. | |
| 2023/0000737 A1 | 1/2023 | Ftouni et al. | |

FOREIGN PATENT DOCUMENTS

| | | |
|---|---|---|
| CN | 101406429 A | 4/2009 |
| CN | 106795005 A | 5/2017 |
| CN | 106852724 A | 6/2017 |
| CN | 107383460 A | 11/2017 |
| CN | 108938450 A | 12/2018 |
| CN | 110409218 A | 11/2019 |
| CN | 110485199 A | 11/2019 |
| EP | 2264108 A1 | 12/2010 |
| EP | 2264109 A1 | 12/2010 |
| EP | 2371766 A1 | 10/2011 |
| EP | 2447213 A1 | 5/2012 |
| EP | 2524898 A1 | 11/2012 |
| EP | 2840065 A1 | 2/2015 |
| EP | 3360601 A1 | 8/2018 |
| GB | 544907 | 5/1942 |
| GB | 548197 | 9/1942 |
| JP | 2010030980 A | 2/2010 |
| JP | 2011236182 A | 11/2011 |
| WO | 9522253 | 8/1995 |
| WO | 0039222 A1 | 7/2000 |
| WO | 2004083316 A1 | 9/2004 |
| WO | 2005121257 A2 | 12/2005 |
| WO | 2009074492 A1 | 6/2009 |

(Continued)

OTHER PUBLICATIONS

International Search Report and Written Opinion issued in PCT/ EP2021/061566 mailed Jul. 28, 2021.
Yuanyuan Li et al., "Encapsulating TiO2 in Lignin-Based Colloidal Spheres for High Sunscreen Performance and Weak Photocatalytic Activity," ACS Sustainable Chemistry & Engineering, vol. 7, No. 6, Feb. 18, 2019, pp. 6234-6242.
Srinivasa Rao Yearla & Kollipara Padmasree (2016) Preparation and characterisation of lignin nanoparticles: evaluation of their potential as antioxidants and UV protectants, Journal of Experimental Nanoscience, 11 :4, 289-302.
Bilal et al., "Exploring the potential of ligninolytic armory for lignin valorization—A way forward for sustainable and cleaner production ", Jour Cleaner Prod, 2021, 326, 129420, pp. 1-14 (Year: 2021).

(Continued)

*Primary Examiner* — Brian Gulledge
(74) *Attorney, Agent, or Firm* — Heslin Rothenberg Farley & Mesiti P.C.

(57)          ABSTRACT

The present invention refers to a dry composition for chemical and physical sun protection, the composition comprising at least one mineral material selected from the group consisting of surface reacted calcium carbonate and/or hydromagnesite, and from 0.1 wt.-% to 100 wt.-%, based on the dry weight of the at least one mineral material of at least one lignin. Furthermore, the present invention refers to an emulsion comprising the inventive dry composition as well as the use of the inventive emulsion for chemical and physical sun protection in a cosmetic formulation.

18 Claims, 2 Drawing Sheets

(56) References Cited

FOREIGN PATENT DOCUMENTS

| WO | 2013142473 A1 | 9/2013 |
| WO | 2017197530 A1 | 11/2017 |

OTHER PUBLICATIONS

Li Zhongzheng, et al.; Chemistry of Plant Fiber Resources; China Light Industry Press (pp. 130-132, published on Jun. 30, 2012).

Li Jian; Wood Science; Higher Education Press, published on Aug. 31, 2002.

Yu et al., "Facile and Green Preparation of High UV-Blocking Lignin/Titanium Dioxide Nanocomposites for Developing Natural Sunscreens", Ind Eng Chem Res, 2018, 57, 15740-15748. (Year: 2018).

Gordobil et al., "Potential use of kraft and organosolv lignins as a natural additive for healthcare products", RSC Adv, 2018, 8, 24525 -24533 (Year: 2018).

M. Morsella et al., "Lignin coating to quench photocatalytic activity of titanium dioxide nanoparticles for potential skin care applications," Rcs Advances, Jan. 1, 2015, vol. 5, No. 71, p. 57453-57461.

Youngjun Kim et al.; Scientific Reports; All Biomass and UV Protective Composite Composed of Compatibilized Lignin and Poly (Lactic-acid); Published: Mar. 8, 2017; Scientific Reports: 7:43596 | DOI: 10. 1038/srep43596; pp. 1-11.

Yong Qian et al., "Lignin: a nature-inspired sun blocker for broa ●●spectrum sunscreens," Green Chemistry, Jan. 1, 2015, vol. 17, No. 1, pp. 320-324.

* cited by examiner

DRY COMPOSITIONS AND/OR EMULSIONS FOR CHEMICAL AND PHYSICAL SUN PROTECTION AND USE THEREOF

CROSS REFERENCE TO RELATED APPLICATIONS

This application is a U.S. National Phase filing under 35 U.S.C. § 371 of International Application PCT/EP2021/061566, filed May 3, 2021, and published as WO 2021/224182 A1 on Nov. 11, 2021. PCT/EP2021/061566 claims priority from European patent application number 20172715.3, filed May 4, 2020. The entire contents of each of these prior applications are hereby incorporated herein by reference.

The present invention refers to a dry composition for chemical and physical sun protection, the composition comprising at least one mineral material selected from the group consisting of surface reacted calcium carbonate and/or hydromagnesite, and from 0.1 wt.-% to 100 wt.-%, based on the dry weight of the at least one mineral material of at least one lignin. Furthermore, the present invention refers to an emulsion comprising the inventive dry composition as well as the use of the inventive emulsion for chemical and physical sun protection in a cosmetic formulation and a preparation method for the dry composition.

It is well known that the sunlight energy and mainly the ultraviolet portion of the sun's spectrum has a damaging effect on living cells, especially on plants and parts thereof as well as on the human skin. In particular, the ultraviolet A (UV-A) radiation which ranges from >320 to 400 nm and ultraviolet B (UV-B) radiation which ranges from 280 to 320 nm have a damaging effect on the human DNA by the formation of free radicals and other reactive species developed through phototoxic reactions in the epidermis and dermis of the skin. As a consequence, the UV-A and UV-B radiation is now considered as a main factor in the development of chronic light-induced alterations such as premature ageing of the skin and development of skin cancer.

Therefore, it is becoming increasingly important to protect living cells from sunburn. Especially, the human skin which is exposed to sun light has to be protected against UV-B as well as UV-A radiation. In the art several attempts have been made to provide such UV protection.

One attempt to reduce the probability of sunburn is the using of mineral particles, usually clay or calcium carbonate, which form a film on the human skin and protect the living cells by reflecting or absorbing the damaging UV radiation. Therefore, these compounds are known as physical sun protecting agents. Such sunscreen compositions are known, for example from US20120052187 A1 that refers to a sunscreen composition comprising Titanium Dioxide (TiO2), Zinc Oxide (ZnO), Silicon Dioxide (SiO2), a surfactant/wetting/dispersant agent (SWD) and water. The composition forms a suspension concentrate that when diluted in water provides a solution that provides uniform coverage using conventional spraying equipment.

US2017333301 A1 refers to a water-in-oil emulsion sunscreen cosmetic comprising 6 to 40 mass % of a UV protective agent; an organic-modified clay mineral; an oil-phase-thickening agent, and a silicone-based surfactant having an HLB (hydrophilic-lipophilic balance) of less than 8. The UV-protective agent may be particles of metal oxides such as zinc oxide, titanium oxide, iron oxide, cerium oxide, and tungsten oxide.

Inorganic UV filters such as zinc oxide and titanium dioxide are photostable and give a broad spectrum protection covering UV-A and UV-B by blocking the UV light. So-called mineral-only sunscreen formulations, i.e. sunscreen formulations comprising solely inorganic UV filter materials such as zinc oxide and/or titanium dioxide were long time especially recommended for people with sensitive skin as well as for babies and toddlers. However, the inorganic UV filters are mostly used in the form of nano particles and it is speculated recently that these nano particles might have harmful effects on the nature and the human health.

US2016312031 A1 refers to inorganic/lignin type polymer composite nanoparticles, a preparation method therefore and application thereof. The preparation method includes adding an activating agent into a basic alkaline lignin solution and then adding a carboxylating agent and reacting to obtain a carboxylated alkaline lignin; dissolving a phosphorylating agent into water, adding epichlorohydrin, and reacting to obtain a hydroxyl phosphate type compound; mixing the carboxylated alkaline lignin and the hydroxyl phosphate type compound and reacting to obtain a lignin type polymer; adding an inorganic nanoparticle suspension into the lignin type polymer and adding an acid to obtain the product after aging and drying.

Another option to reduce the probability of sunburn is the using of organic UV filters. Organic UV filters are often transparent or translucent. Such filters provide chemical sun protection by absorbing the UV-A and/or UV-B radiation. Organic UV filters can be classified in synthetically produced UV filters and natural occurring UV filters. Synthetically produced UV filters do not occur in nature but are produced synthetically whereas natural occurring UV filters occur in nature or are produced from natural occurring compounds.

EP3360601 A1 relates to a cosmetic composition having UV-A and/or UV-B protection comprising at least one inorganic UV filter, and surface-reacted calcium carbonate having a volume median particle size d50 from 0.1 to 90 μm, wherein the surface-reacted calcium carbonate is a reaction product of natural ground calcium carbonate or precipitated calcium carbonate with carbon dioxide and one or more H3O+ ion donors, wherein the carbon dioxide is formed in situ by the H3O+ ion donors treatment and/or is supplied from an external source.

Synthetically produced UV filters such as, for example, octocrylene can be designed such that they perfectly match with the respective system or composition they are blended with. Additionally, such filters can be customized for the individual application. However, synthetic organic UV filters, for example, such as octocrylene are subject to continuously increasing concerns especially because they are suspected to be a possible cause of skin irritations and allergies in sensitive persons and their potentially harmful effect on the environment.

Therefore, there is a continuous need in the art for adequate formulations or compositions providing sufficient or improved UV-B and/or UV-A protection to living cells especially to the human skin.

Thus, it is an objective of the present invention to provide a composition for providing chemical and physical sun protection. More precisely, it is an objective of the present invention to provide a composition for providing sufficient or improved UV-B and/or UV-A protection to living cells, especially to human skin by different mechanisms, namely by reflecting the UV-B and/or UV-A radiation as well as by absorbing the UV-B and/or UV-A radiation. A further object of the present invention is that the compounds used in these compositions are non-toxic to humans, do not provide a harmful effect on the environment and might be used in cosmetic applications. Another object of the present invention is that the compositions should be easily and quickly produced, cheap and especially easy to handle. It is especially preferred that the compositions stick to the human skin and do not get washed off easily by rain or sweat. Additionally, the compositions should be usable in combination with inorganic or organic UV filters. Preferably, the amount of these UV filters can be reduced and the compositions still having the same or improved chemical and physical sun protection.

These and other objectives of the present invention can be solved by a composition for chemical and physical sun protection as described in the present invention and defined in the claims. Advantageous embodiments of the invention are defined in the corresponding sub-claims.

Figure 1:
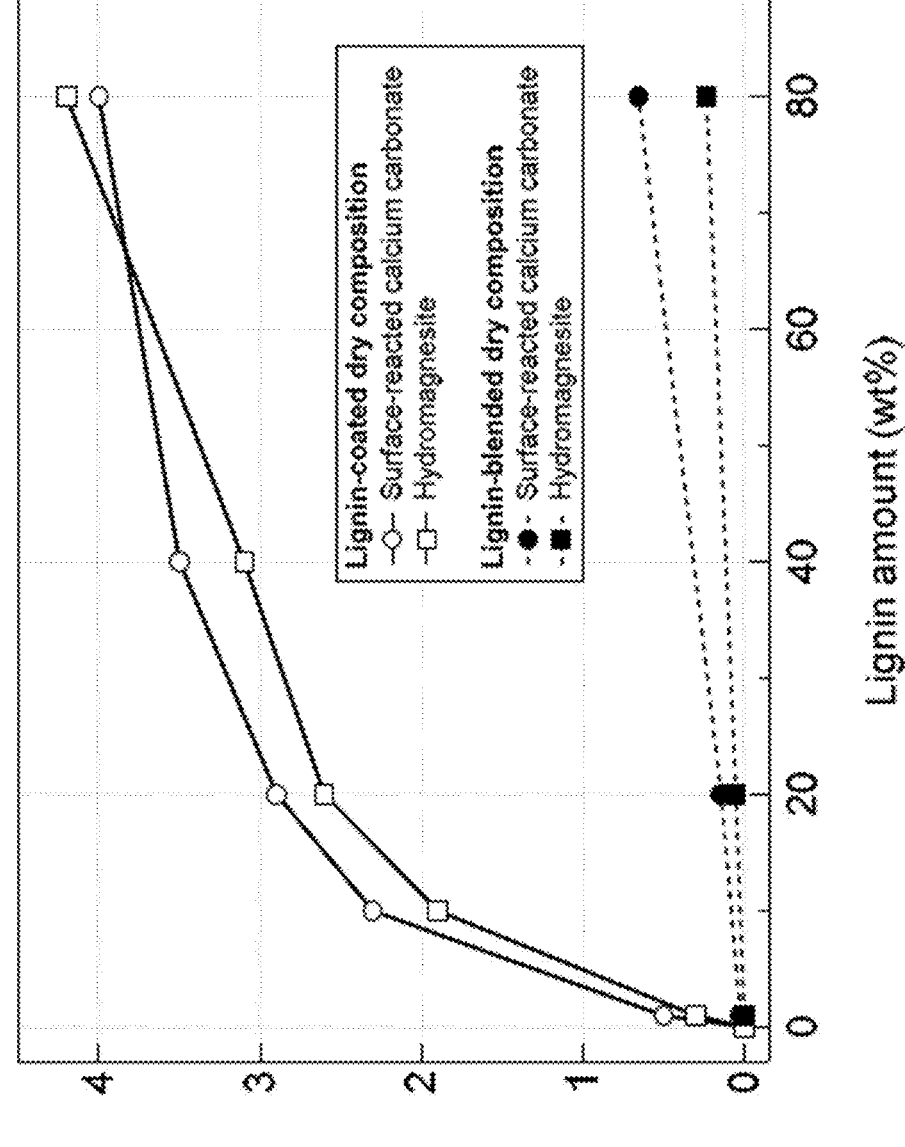
FIG. 1 shows the Kubelka-Munk function evaluated at 300 nm wavelength as a function of the lignin content coated on or blended with the at least one mineral material.

According to one embodiment of the present invention, a dry composition for chemical and physical sun protection is provided, the composition comprising a) at least one mineral material selected from the group consisting of surface reacted calcium carbonate and/or hydromagnesite, wherein the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source and b) from 0.1 wt.-% to 100 wt.-%, based on the dry weight of the at least one mineral material of step a) of at least one lignin.

The inventors surprisingly found out that the foregoing composition provides sufficient or improved chemical and physical sun protection. More precisely, the inventors surprisingly found out that the inventive composition offers two different mechanisms for UV-B and/or UV-A protection to living cells, especially to human skin by different mechanisms, namely by reflecting the UV-B and/or UV-A radiation as well as by absorbing the UV-B and/or UV-A radiation. Furthermore, the compounds used in the inventive composition, namely the surface reacted calcium carbonate and/or hydromagnesite and the lignin are non-toxic to humans and do not provide a harmful effect on the environment. Often these compounds might be used in cosmetic applications. Furthermore, the inventors surprisingly found that the compositions of the present invention can be easily and quickly produced, are cheap and especially easy to handle.

Additionally, if the present compositions are used in combination with known inorganic or organic UV filters the amount of these UV filters might be reduced and the compositions might still have the same or improved chemical and physical sun protection.

Furthermore, if the emulsions of the present invention having chemical and physical sun protection are used in cosmetic formulations these compositions might have improved appearance and/or sensory properties. Especially, these cosmetic formulations might show a reduced whitening effect when applied to the skin. Furthermore, these cosmetic formulations can be easily applied to the skin and form an even and uniform film on the skin. Moreover, such a cosmetic formulation might be less greasy and sticky, might exhibit a good spreadability and might dry fast.

According to another aspect of the present invention, an emulsion for chemical and physical sun protection is provided, the emulsion comprising a water in oil or oil in water mixture and 0.1 to 40 wt.-% of the inventive dry composition, based on the weight of the water in oil or oil in water mixture.

According to another aspect of the present invention, the inventive emulsion for chemical and physical sun protection is used in a cosmetic formulation.

According to another aspect of the present invention a method for preparing the inventive dry composition for chemical and physical sun protection is provided. The method comprises the steps of i) providing at least one organic solvent and/or at least one aqueous solution having a pH≥10, ii) providing at least one lignin, iii) providing at least one mineral material selected from the group consisting of surface reacted calcium carbonate and/or hydromagnesite, wherein the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source, iv) mixing, in any order, the at least one organic solvent and/or at least one aqueous solution of step i) with the lignin of step ii), to obtain a lignin solution, v) mixing, in any order, the lignin solution obtained in step iv) with the at least one mineral material of step iii) in an amount such that the amount of dry lignin is 0.1 wt.-% to 100 wt.-%, based on the dry weight of the at least one mineral material and vi) drying the suspension obtained in step v) to obtain the dry composition according to claims 1 to 12.

Advantageous embodiments of the above aspects are defined in the corresponding sub-claims.

According to one embodiment of the present invention, the at least one mineral material is surface reacted calcium carbonate and/or the surface reacted calcium carbonate has a) a volume median particle size $d_{50}$ from 0.1 to 90 μm, preferably from 0.1 to 75 μm, more preferably from 0.5 to 50 μm, even more preferably from 1 to 40 μm and most preferably from 1.5 to 15 μm and/or b) a volume top cut ($d_{98}$) of ≤100 μm, preferably ≤60 μm, more preferably ≤45 μm and most preferably ≤20 μm, and/or c) a specific surface area (BET) of from 10 to 200 m²/g, preferably from 20 to 180 m²/g, even more preferably from 25 to 160 m²/g and most preferably from 30 to 140 m²/g, measured using nitrogen and the BET method according to ISO 9277:2010.

According to another embodiment of the present invention, the at least one mineral material is hydromagnesite and/or the hydromagnesite has a) a volume median particle size $d_{50}$ from 1 to 75 μm, preferably from 1.2 to 50 μm, more preferably from 1.5 to 30 μm, even more preferably from 1.7 to 15 μm and most preferably from 1.9 to 10 μm and/or b) a volume top cut ($d_{98}$) of ≤100 μm, preferably ≤60 μm, more preferably ≤45 μm and most preferably ≤20 μm, and/or c) a specific surface area (BET) of from 25 to 200 m²/g, preferably from 30 to 150 m²/g, even more preferably from 32 to 120 m²/g and most preferably from 35 to 100 $m^2/g$, measured using nitrogen and the BET method according to ISO 9277:2010.

According to another embodiment of the present invention, the at least one lignin is a water soluble or water insoluble lignin selected from the group consisting of natural lignin, klason lignin, hydrolyzed lignin, milled wood lignin, soda lignin, organosolv lignin, kraft lignin, sulphonated lignin and mixtures thereof, preferably is a water-insoluble lignin selected from the group consisting of klason lignin, kraft lignin and mixtures thereof and most preferably is kraft lignin.

According to another embodiment of the present invention, the at least one lignin is present in the composition in an amount from 1 to 80 wt.-%, based on the dry weight of the at least one mineral material of step a), preferably in an amount of 2 to 50 wt.-%, even more preferably in an amount of 3 to 30 wt.-% and most preferably in an amount of 5 to 25 wt.-%.

According to another embodiment of the present invention, the composition further comprises an organic solvent, preferably in an amount of 0.1 to 200 wt.-%, based on the dry weight of the at least one mineral material of step a), more preferably in an amount of 0.5 to 100 wt.-%, even more preferably in an amount of 0.75 to 50 wt.-% and most preferably in an amount of 1 to 25 wt.-% and/or preferably in an amount of 100 to 500 wt.-%, based on the dry weight of the at least one lignin of step b), more preferably in an amount of 150 to 450 wt.-% and most preferably in an amount of 200 to 300 wt.-%.

According to another embodiment of the present invention, the organic solvent is selected from the group consisting of hexane, toluene, methanol, ethanol, dioxane, acetone, dimethyl sulfoxide, dimethylformamide, ethylene glycol, ethylacetate, glycerol, γ-valerolactone, polyethylene glycol, polypropylene glycol and mixtures thereof, more preferably is selected from the group consisting of ethylene glycol, ethylacetate, glycerol, γ-valerolactone, polyethylene glycol, polypropylene glycol and mixtures thereof, and most preferably is γ-valerolactone.

According to another embodiment of the present invention, the composition further comprises at least one inorganic UV filter selected from the group consisting of titanium dioxide, zinc oxide, iron oxide, cerium oxide, calcium-doped cerium oxide, cerium phosphate, and mixtures thereof, preferably the least one inorganic UV filter is selected from the group consisting of titanium dioxide, zinc oxide, and mixtures thereof, more preferably the at least one inorganic UV filter is titanium dioxide and/or zinc oxide, and most preferably the at least one inorganic UV filter is titanium dioxide.

According to another embodiment of the present invention, the composition further comprises at least one organic UV filter, preferably the at least one organic UV filter is selected from the group consisting of derivatives of cinnamic acid and its salts, derivatives of salicylic acid and its salts, benzophenones, derivatives of aminobenzoic acid and its salts, dibenzoylmethanes, benzylidenecamphor derivatives, benzimidazole derivatives, diphenylacrylate derivatives, acrylamide derivatives, benzotriazole derivatives, triazine derivatives, benzalmalonate derivatives, aminobenzoate derivatives, octocrylene, and mixtures thereof, and more preferably the at least one organic UV filter is selected from the group consisting of derivatives of cinnamic acid and its salts, benzophenones, octocrylene, and mixtures thereof.

According to another embodiment of the present invention the composition further comprises at least one salt, preferably the at least one salt comprises ammonium carbonate, sodium carbonate, calcium salts, magnesium salts or mixtures thereof.

According to another embodiment of the present invention, the at least one lignin is present in the composition in the form of a mixture with or a coating on the at least one mineral material, and preferably is present as a coating on the at least one mineral material.

According to another embodiment of the present invention, the at least one lignin in the coating on the at least one mineral material is a water insoluble lignin, and preferably kraft lignin.

According to another embodiment of the present invention, when the inventive emulsion for chemical and physical sun protection is used in a cosmetic formulation, the at least one lignin is present in the form of a coating on the at least one mineral material and/or wherein the at least one lignin is a water-insoluble lignin, preferably kraft lignin.

According to another embodiment of the present invention, the cosmetic formulation is a sunscreen product, facial makeup product, hair care product, hand care product, skin care product, body care product or mixtures thereof.

According to another embodiment of the present invention, the aqueous solution in step i) has a pH≥10, preferably between 10.5 and 13.5, even more preferably between 11.0 and 13.0 and most preferably between 11.5 and 12.5 and/or the aqueous solution comprises caustic soda, ammonia solution, sodium hydroxide, potassium hydroxide, lye, sodium carbonate, calcium hydroxide, magnesium hydroxide and mixtures thereof and more preferably is ammonia solution.

According to another embodiment of the present invention, the drying in step vi) is performed at temperatures above 75° C., preferably between 75° C. and 250° C., more preferably between 100 and 230° C., more preferably between 110 and 200° C. and most preferably between 120 and 180° C.

It should be understood that for the purposes of the present invention, the following terms have the following meanings:

"Chemical sun protection" in the meaning of the present invention, refers to the protection of UV-B and/or UV-A radiation by absorbing the UV-B and/or UV-A radiation.

"Physical sun protection" in the meaning of the present invention, refers to the protection of UV-B and/or UV-A radiation by reflecting the UV-B and/or UV-A radiation.

"UV-B protection" and "UV-A protection" in the meaning of the present invention, refers to the protection from ultraviolet B (UV-B) radiation which ranges from 280 to 320 nm and the ultraviolet A (UV-A) radiation which ranges from >320 to 400 nm, both cause sunburn to human skin.

"Water-insoluble" materials are defined as materials which, when 100 g of said material is mixed with 100 g deionized water and filtered on a filter having a 0.2 μm pore size at 20° C. under atmospheric pressure to recover the liquid filtrate, provide less than or equal to 0.1 g of recovered solid material following evaporation at 95 to 100° C. of 100 g of said liquid filtrate at ambient pressure. "Water-soluble" materials are thus defined as materials which, when 100 g of said material is mixed with 100 g deionized water and filtered on a filter having a 0.2 μm pore size at 20° C. under atmospheric pressure to recover the liquid filtrate, provide more than 0.1 g of recovered solid material following evaporation at 95 to 100° C. of 100 g of said liquid filtrate at ambient pressure.

A "surface-reacted calcium carbonate" according to the present invention is a reaction product of ground natural calcium carbonate (GNCC) or precipitated calcium carbonate (PCC) treated with carbon dioxide and one or more $H_3O+$ ion donors, wherein the carbon dioxide is formed in situ by the $H_3O+$ ion donors treatment and/or is supplied from an external source. A $H_3O+$ ion donor in the context of the present invention is a Brønsted acid and/or an acid salt.

An "$H_3O+$ ion donor" in the context of the present invention is a Brønsted acid and/or an acid salt, i.e. a salt containing an acidic hydrogen. The term "acid" as used herein refers to an acid in the meaning of the definition by Brønsted and Lowry (e.g., $H_2SO_4$, $HSO_4-$). The term "free acid" refers only to those acids being in the fully protonated form (e.g., $H_2SO_4$).

The term "hydromagnesite" or "basic magnesium carbonate" according to the present invention is a naturally occurring mineral which is found, for example, in magnesium rich minerals such as serpentine and altered magnesium rich igneous rocks, or a synthetically prepared material. Hydromagnesite is described as having the chemical formula $Mg_5(CO_3)_4(OH)_2 \cdot 4H_2O$.

The term "ground calcium carbonate" (GCC) or "ground natural calcium carbonate" (GNCC) as used herein refers to a particulate material obtained from natural calcium carbonate-containing minerals (e.g. chalk, limestone, marble or dolomite) which has been processed in a wet and/or dry comminution step, such as crushing and/or grinding, and optionally has been subjected to further steps such as screening and/or fractionation, for example, by a cyclone or a classifier.

A "precipitated calcium carbonate" (PCC) in the meaning of the present invention is a synthesized material, obtained by precipitation following a reaction of carbon dioxide and calcium hydroxide (hydrated lime) in an aqueous environment. Alternatively, precipitated calcium carbonate can also be obtained by reacting calcium- and carbonate salts, for example calcium chloride and sodium carbonate, in an aqueous environment. PCC may have a vateritic, calcitic or aragonitic crystalline form. PCCs are described, for example, in EP2447213 A1, EP2524898 A1, EP2371766 A1, EP2840065 A1, or WO2013142473 A1.

The "particle size" of particulate materials other than surface-reacted calcium carbonate and hydromagnesite (e.g., GCC or PCC) herein is described by its distribution of particle sizes $dx(wt)$. Therein, the value $dx(wt)$ represents the diameter relative to which x % by weight of the particles have diameters less than $dx(wt)$. This means that, for example, the $d20(wt)$ value is the particle size at which 20 wt. % of all particles are smaller than that particle size. The $d50(wt)$ value is thus the weight median particle size, i.e. 50 wt. % of all particles are smaller than that particle size and the $d98(wt)$ value, referred to as weight-based top cut, is the particle size at which 98 wt. % of all particles are smaller than that particle size. The weight-based median particle size $d50(wt)$ and top cut $d98(wt)$ are measured by the sedimentation method, which is an analysis of sedimentation behaviour in a gravimetric field. The measurement is made with a Sedigraph™ 5120 of Micromeritics Instrument Corporation, USA. The method and the instrument are known to the skilled person and are commonly used to determine particle size distributions. The measurement is carried out in an aqueous solution of 0.1 wt. % $Na_4P_2O_7$. The samples are dispersed using a high speed stirrer and sonication.

The "particle size" of surface-reacted calcium carbonate and hydromagnesite herein is described as volume-based particle size distribution $dx(vol)$. Therein, the value $dx(vol)$ represents the diameter relative to which x % by volume of the particles have diameters less than $dx(vol)$. This means that, for example, the $d20(vol)$ value is the particle size at which 20 vol. % of all particles are smaller than that particle size. The $d50(vol)$ value is thus the volume median particle size, i.e. 50 vol. % of all particles are smaller than that particle size and the $d98(vol)$ value, referred to as volume-based top cut, is the particle size at which 98 vol. % of all particles are smaller than that particle size. The volume-based median particle size $d50(vol)$ and top cut $d98(vol)$ are evaluated using a Malvern Mastersizer 2000 Laser Diffraction System (Malvern Instruments Plc., Great Britain). The raw data obtained by the measurement is analyzed using the Mie theory, with a particle refractive index of 1.57 and an absorption index of 0.005//using the Fraunhofer theory. The methods and instruments are known to the skilled person and are commonly used to determine particle size distributions.

A "specific surface area (SSA)" of a calcium carbonate-containing filler material in the meaning of the present invention is defined as the surface area of the calcium carbonate-containing filler material divided by its mass. As used herein, the specific surface area is measured by nitrogen gas adsorption using the BET isotherm (ISO 9277:2010) and is specified in $m^2/g$.

For the purpose of the present invention the "porosity" or "pore volume" refers to the intra-particle intruded specific pore volume. Said porosity or pore volume is measured using a Micromeritics Autopore V 9620 mercury porosimeter.

The term "dry" material or "dry" composition, is understood to be a material/composition having less than 5.0% by weight of water relative to the material/composition weight. The % water (equal to residual total moisture content) is determined according to the Coulometric Karl Fischer measurement method, wherein the material/composition is heated to 220° C., and the water content released as vapour and isolated using a stream of nitrogen gas (at 100 ml/min) is determined in a Coulometric Karl Fischer unit.

The term "solid" according to the present invention refers to a material that is solid under standard ambient temperature and pressure (SATP) which refers to a temperature of 298.15 K (25° C.) and an absolute pressure of exactly 1 bar. The solid may be in the form of a powder, tablet, granules, flakes etc. Accordingly, the term "liquid medium" refers to a material that is liquid under standard ambient temperature and pressure (SATP) which refers to a temperature of 298.15 K (25° C.) and an absolute pressure of exactly 1 bar.

A "salt" in the meaning of the present invention refers to a chemical compound consisting of an ionic assembly of cations and anions and is composed of related numbers of cations (positively charged ions) and anions (negatively charged ions) so that the product is electrically neutral (without a net charge).

A "coating" in the meaning of the present invention means that one compound is located on the surface of another compound.

A "suspension" or "slurry" in the meaning of the present invention refers to a mixture comprising at least one insoluble solid in a liquid medium, for example water, and optionally further additives, and usually contains large amounts of solids and, thus, is more viscous (higher viscosity) and can have a higher density than the liquid medium from which it is formed.

Where the term "comprising" or "containing" is used in the present description and claims, it does not exclude other elements. For the purposes of the present invention, the term "consisting of" is considered to be a preferred embodiment of the term "comprising of". If hereinafter a group is defined to comprise at least a certain number of embodiments, this is also to be understood to disclose a group, which preferably consists only of these embodiments.

Where an indefinite or definite article is used when referring to a singular noun, e.g. "a", "an" or "the", this includes a plural of that noun unless something else is specifically stated.

Terms like "obtainable" or "definable" and "obtained" or "defined" are used interchangeably. This e.g. means that, unless the context clearly dictates otherwise, the term "obtained" does not mean to indicate that, e.g. an embodiment must be obtained by e.g. the sequence of steps following the term "obtained" even though such a limited understanding is always included by the terms "obtained" or "defined" as a preferred embodiment.

In the following, the details and preferred embodiments of the present inventive will be described in more detail. Embodiments that refer to the composition and emulsion will also refer to the use of the inventive emulsion for chemical and physical sun protection in a cosmetic formulation and vice versa.

According to the present invention a dry composition for chemical and physical sun protection is provided, the composition comprising a) at least one mineral material selected from the group consisting of surface reacted calcium carbonate and/or hydromagnesite, wherein the surface-reacted calcium carbonate is a reaction product of natural ground calcium carbonate or precipitated calcium carbonate with carbon dioxide and one or more H3O+ ion donors, wherein the carbon dioxide is formed in situ by the H3O+ ion donors treatment and/or is supplied from an external source and b) from 0.1 wt.-% to 100 wt.-%, based on the dry weight of the at least one mineral material of step a) of at least one lignin.

The at Least One Mineral Material

The at least one mineral material is selected from the group consisting of surface reacted calcium carbonate and/or hydromagnesite.

The term "at least one" mineral material in the meaning of the present invention means that the mineral material comprises, preferably consists of, one or more mineral material(s).

In one embodiment of the present invention, the at least one mineral material in the composition comprises, preferably consists of, one mineral material, for example surface reacted calcium carbonate or hydromagnesite. Alternatively, the at least one mineral material comprises, preferably consists of, two or more mineral materials, for example, two or more surface reacted calcium carbonates or two or more hydromagnesites or surface reacted calcium carbonate and hydromagnesite. For example, the at least one mineral material comprises, preferably consists of, two or three mineral material.

Preferably, the at least one mineral material in the composition comprises, more preferably consists of, one mineral material. According to a preferred embodiment the mineral material is surface reacted calcium carbonate.

A "surface reacted mineral material" in the meaning of the present invention is a reaction product of natural ground calcium carbonate (GNCC) or precipitated calcium carbonate (PCC) with carbon dioxide and one or more H3O+ ion donors, wherein the carbon dioxide is formed in situ by the H3O+ ion donors treatment and/or is supplied from an external source. The surface-reacted calcium carbonate (SRCC) is also referred to as modified calcium carbonate (MCC).

It is appreciated that the surface-reacted calcium carbonate can be one or a mixture of different kinds of surface-reacted calcium carbonate(s). In one embodiment of the present invention, the surface-reacted calcium carbonate comprises, preferably consists of, one kind of surface-reacted calcium carbonate. Alternatively, the surface-reacted calcium carbonate comprises, preferably consists of, two or more kinds of surface-reacted calcium carbonates. For example, the surface-reacted calcium carbonate comprises, preferably consists of, two or three kinds of surface-reacted calcium carbonates. Preferably, the surface-reacted calcium carbonate comprises, more preferably consists of, one kind of surface-reacted calcium carbonate.

The surface-reacted calcium carbonate is a reaction product of natural ground calcium carbonate (GNCC) or precipitated calcium carbonate (PCC) treated with carbon dioxide and one or more H3O+ ion donors, wherein the carbon dioxide is formed in situ by the H3O+ ion donors treatment and/or is supplied from an external source. Because of the reaction of natural ground calcium carbonate or precipitated calcium carbonate with carbon dioxide and the one or more H3O+ ion donors, surface-reacted calcium carbonate may comprise GNCC or PCC and at least one water-insoluble calcium salt other than calcium carbonate.

In a preferred embodiment, said surface-reacted calcium carbonate comprises GNCC or PCC and at least one water-insoluble calcium salt other than calcium carbonate which is present on at least part of the surface of said GNCC or PCC.

An H3O+ ion donor in the context of the present invention is a Brønsted acid and/or an acid salt.

In a preferred embodiment of the invention, the surface-reacted calcium carbonate is obtained by a process comprising the steps of:
(a) providing a suspension of ground natural calcium carbonate (GNCC) or precipitated calcium carbonate (PCC);
(b) adding at least one acid having a pK$_a$ value of 0 or less at 20° C., or having a pK$_a$ value from 0 to 2.5 at 20° C. to the suspension provided in step (a); and
(c) treating the suspension provided in step (a) with carbon dioxide before, during or after step (b).

According to another embodiment, the surface-reacted calcium carbonate is obtained by a process comprising the steps of:
(a) providing a ground natural calcium carbonate (GNCC) or precipitated calcium carbonate (PCC);
(b) providing at least one water-soluble acid;
(c) providing gaseous carbon dioxide; and
(d) contacting said GNCC or PCC provided in step (a), the at least one acid provided in step (b) and the gaseous carbon dioxide provided in step (c);
characterized in that
(i) the at least one acid provided in step (b) has a pK$_a$ of greater than 2.5 and less than or equal to 7 at 20° C., associated with the ionisation of its first available hydrogen, and a corresponding anion is formed on loss of this first available hydrogen capable of forming a water-soluble calcium salt; and
(ii) following contacting the at least one water-soluble acid provided in step (b) and the GNCC or PCC provided in step (a), at least one water-soluble salt, which in the case of a hydrogen-containing salt has a pK$_a$ of greater than 7 at 20° C., associated with the ionisation of the first available hydrogen, and the salt anion of which is capable of forming water-insoluble calcium salts, is additionally provided.

The source of calcium carbonate, e.g., ground natural calcium carbonate (GNCC), preferably is selected from calcium carbonate-containing minerals selected from the group consisting of marble, chalk, limestone and mixtures thereof. Natural calcium carbonate may comprise further naturally occurring components such as alumino silicate etc. According to one embodiment, natural calcium carbonate, such as GNCC, comprises aragonitic, vateritic or calcitic mineralogical crystal forms of calcium carbonate or mixtures thereof.

In general, the grinding of ground natural calcium carbonate may be performed in a dry or wet grinding process and may be carried out with any conventional grinding device known to the skilled person, for example, under conditions such that comminution predominantly results from impacts with a secondary body. In case the ground natural calcium carbonate comprises wet ground calcium carbonate, the grinding step may be performed under conditions such that autogenous grinding takes place and/or by horizontal ball milling, and/or other such processes known to the skilled person. The wet processed ground natural calcium carbonate thus obtained may be washed and dewatered by well-known processes prior to drying. The subsequent step of drying (if necessary) may be carried out in a single step such as spray drying, or in at least two steps. It is also common that such a mineral material undergoes a beneficiation step to remove impurities.

As already indicated hereinabove, a precipitated calcium carbonate (PCC) in the meaning of the present invention is a synthesized material, generally obtained by precipitation following a reaction of carbon dioxide and calcium hydroxide in an aqueous environment or by precipitation of calcium and carbonate ions, for example CaCl2 and Na2CO3, out of solution. Further possible ways of producing PCC are the lime soda process, or the Solvay process in which PCC is a by-product of ammonia production. Precipitated calcium carbonate exists in three primary crystalline forms: calcite, aragonite and vaterite, and there are many different polymorphs (crystal habits) for each of these crystalline forms. Calcite has a trigonal structure with typical crystal habits such as scalenohedral (S-PCC), rhombohedral (R-PCC), hexagonal prismatic, pinacoidal, colloidal (C-PCC), cubic, and prismatic (P-PCC). Aragonite is an orthorhombic structure with typical crystal habits of twinned hexagonal prismatic crystals, as well as a diverse assortment of thin elongated prismatic, curved bladed, steep pyramidal, chisel shaped crystals, branching tree, and coral or worm-like form. Vaterite belongs to the hexagonal crystal system. The obtained aqueous PCC slurry can be mechanically dewatered and dried.

According to one embodiment of the present invention, the precipitated calcium carbonate comprises aragonitic, vateritic or calcitic mineralogical crystal forms of calcium carbonate or mixtures thereof.

Precipitated calcium carbonate may be ground prior to the treatment with carbon dioxide and at least one H3O+ ion donor by the same means as used for grinding natural calcium carbonate and described above.

According to one embodiment of the present invention, the natural or precipitated calcium carbonate is in form of particles having a weight median particle size d50(wt) of from 0.1 to 90 μm, preferably from 0.1 to 75.0 μm, more preferably from 0.5 to 50.0 μm, even more preferably from 1 to 40.0 μm, even more preferably from 1.2 to 30 μm and most preferably from 1.5 to 15 μm. According to a further embodiment of the present invention, the natural or precipitated calcium carbonate is in form of particles having a top cut particle size d98(wt) of from 0.2 to 150 μm, preferably from 1 to 100 μm, more preferably from 2 to 80 μm, even more preferably from 2.4 to 60 μm, and most preferably from 3 to 30 μm.

The natural or precipitated calcium carbonate may be used dry or suspended in water. Preferably, a corresponding aqueous slurry has a content of natural or precipitated calcium carbonate within the range of from 1 to 90 wt. %, more preferably from 3 to 60 wt. %, even more preferably from 5 to 40 wt. %, and most preferably from 10 to 25 wt. %, based on the total weight of said slurry.

The one or more H3O+ ion donor used for the preparation of surface-reacted calcium carbonate may be any strong acid, medium-strong acid, or weak acid, or mixtures thereof, generating H3O+ ions under the preparation conditions. According to the present invention, the at least one H3O+ ion donor can also be an acid salt, generating H3O+ ions under the preparation conditions.

According to one embodiment, the at least one H3O+ ion donor is a strong acid having a pKa of 0 or less at 20° C.

According to another embodiment, the at least one H3O+ ion donor is a medium-strong acid having a pKa value from 0 to 2.5 at 20° C. If the pKa at 20° C. is 0 or less, the acid is preferably selected from sulphuric acid, hydrochloric acid, or mixtures thereof. If the pKa at 20° C. is from 0 to 2.5, the H3O+ ion donor is preferably selected from H2S03, H3PO4, oxalic acid, or mixtures thereof. The at least one H3O+ ion donor can also be an acid salt, for example, HSO4- or H2PO4-, being at least partially neutralized by a corresponding cation such as Li+, Na+ and/or K+, or HPO42-, being at least partially neutralized by a corresponding cation such as Li+, Na+, K+, Mg2+ and/or Ca2+. The at least one H3O+ ion donor can also be a mixture of one or more acids and one or more acid salts.

According to still another embodiment, the at least one H3O+ ion donor is a weak acid having a pKa value of greater than 2.5 and less than or equal to 7, when measured at 20° C., associated with the ionisation of the first available hydrogen, and having a corresponding anion, which is capable of forming water-soluble calcium salts. Subsequently, at least one water-soluble salt, which in the case of a hydrogen-containing salt has a pKa of greater than 7, when measured at 20° C., associated with the ionisation of the first available hydrogen, and the salt anion of which is capable of forming water-insoluble calcium salts, is additionally provided. According to a more preferred embodiment, the weak acid has a pKa value from greater than 2.5 to 5 at 20° C., and more preferably the weak acid is selected from the group consisting of acetic acid, formic acid, propanoic acid and mixtures thereof. Exemplary cations of said water-soluble salt are selected from the group consisting of potassium, sodium, lithium and mixtures thereof. In a more preferred embodiment, said cation is sodium or potassium. Exemplary anions of said water-soluble salt are selected from the group consisting of phosphate, dihydrogen phosphate, monohydrogen phosphate, oxalate, silicate, mixtures thereof and hydrates thereof. In a more preferred embodiment, said anion is selected from the group consisting of phosphate, dihydrogen phosphate, monohydrogen phosphate, mixtures thereof and hydrates thereof. In a most preferred embodiment, said anion is selected from the group consisting of dihydrogen phosphate, monohydrogen phosphate, mixtures thereof and hydrates thereof. Water-soluble salt addition may be performed dropwise or in one step. In the case of dropwise addition, this addition preferably takes place within a time period of 10 min. It is more preferred to add said salt in one step.

According to one embodiment of the present invention, the at least one $H_3O^+$ ion donor is selected from the group consisting of hydrochloric acid, sulphuric acid, sulphurous acid, phosphoric acid, citric acid, oxalic acid, acetic acid, an acidic salt, formic acid and mixtures thereof. Preferably the at least one $H_3O^+$ ion donor is selected from the group consisting of hydrochloric acid, sulphuric acid, sulphurous acid, phosphoric acid, oxalic acid, $H_2PO_4^-$, being at least partially neutralized by a corresponding cation such as $Li^+$, $Na^+$ and/or $K^+$, $HPO_4^{2-}$, being at least partially neutralized by a corresponding cation such as $Li^+$, $Na^+$, $K^+$, $Mg^{2+}$ and/or $Ca^{2+}$ and mixtures thereof, more preferably the at least one acid is selected from the group consisting of hydrochloric acid, sulphuric acid, sulphurous acid, phosphoric acid, oxalic acid, or mixtures thereof. A particularly preferred $H_3O^+$ ion donor is phosphoric acid.

The one or more $H_3O^+$ ion donor can be added to the suspension as a concentrated solution or a more diluted solution. Preferably, the molar ratio of the $H_3O^+$ ion donor to the natural or precipitated calcium carbonate is from 0.01:1 to 4:1, more preferably from 0.02:1 to 2:1, even more preferably from 0.05:1 to 1:1 and most preferably from 0.1:1 to 0.58:1.

In another preferred embodiment, the at least one $H_3O^+$ ion donor is selected from the group consisting of hydrochloric acid, sulphuric acid, sulphurous acid, phosphoric acid, citric acid, oxalic acid, acetic acid, formic acid and mixtures thereof, wherein the molar ratio of the $H_3O^+$ ion donor to the natural or precipitated calcium carbonate is from 0.01:1 to 4:1, more preferably from 0.02:1 to 2:1, even more preferably from 0.05:1 to 1:1 and most preferably from 0.1:1 to 0.58:1.

In another preferred embodiment, the at least one $H_3O^+$ ion donor is a mixture of phosphoric acid and citric acid, more preferably the molar ratio of the $H_3O^+$ ion donor to the natural or precipitated calcium carbonate is from 0.01:1 to 4:1, more preferably from 0.02:1 to 2:1, even more preferably from 0.05:1 to 1:1 and most preferably from 0.1:1 to 0.58:1. In this embodiment, phosphoric acid is preferably used in excess relative to citric acid.

As an alternative, it is also possible to add the $H_3O^+$ ion donor to the water before the natural or precipitated calcium carbonate is suspended.

In a next step, the natural or precipitated calcium carbonate is treated with carbon dioxide. If a strong acid such as sulphuric acid or hydrochloric acid is used for the $H_3O^+$ ion donor treatment of the natural or precipitated calcium carbonate, the carbon dioxide is automatically formed. Alternatively or additionally, the carbon dioxide can be supplied from an external source.

$H_3O^+$ ion donor treatment and treatment with carbon dioxide can be carried out simultaneously which is the case when a strong or medium-strong acid is used. It is also possible to carry out $H_3O^+$ ion donor treatment first, e.g., with a medium strong acid having a pKa in the range of 0 to 2.5 at 20° C., wherein carbon dioxide is formed in situ, and thus, the carbon dioxide treatment will automatically be carried out simultaneously with the $H_3O^+$ ion donor treatment, followed by the additional treatment with carbon dioxide supplied from an external source.

In a preferred embodiment, the $H_3O^+$ ion donor treatment step and/or the carbon dioxide treatment step are repeated at least once, more preferably several times. According to one embodiment, the at least one $H_3O^+$ ion donor is added over a time period of at least about 5 min, preferably at least about 10 min, typically from about 10 to about 20 min, more preferably about 30 min, even more preferably about 45 min, and sometimes about 1 h or more.

Subsequent to the $H_3O^+$ ion donor treatment and carbon dioxide treatment, the pH of the aqueous suspension, measured at 20° C., naturally reaches a value of greater than 6.0, preferably greater than 6.5, more preferably greater than 7.0, even more preferably greater than 7.5, thereby preparing the surface-reacted natural or precipitated calcium carbonate as an aqueous suspension having a pH of greater than 6.0, preferably greater than 6.5, more preferably greater than 7.0, even more preferably greater than 7.5.

In a particular preferred embodiment the surface reacted calcium carbonate is a reaction product of natural ground calcium carbonate (GNCC) with carbon dioxide and phosphoric acid, wherein the carbon dioxide is formed in situ by the phosphoric acid treatment.

Further details about the preparation of the surface-reacted natural calcium carbonate are disclosed in WO0039222 A1, WO2004083316 A1, WO2005121257 A2, WO2009074492 A1, EP2264108 A1, EP2264109 A1 and US20040020410 A1, the content of these references herewith being included in the present document.

Similarly, surface-reacted precipitated calcium carbonate may be obtained. As can be taken in detail from WO2009074492 A1, surface-reacted precipitated calcium carbonate is obtained by contacting precipitated calcium carbonate with $H_3O^+$ ions and with anions being solubilized in an aqueous medium and being capable of forming water-insoluble calcium salts, in an aqueous medium to form a slurry of surface-reacted precipitated calcium carbonate, wherein said surface-reacted precipitated calcium carbonate comprises an insoluble, at least partially crystalline calcium salt of said anion formed on the surface of at least part of the precipitated calcium carbonate.

Said solubilized calcium ions correspond to an excess of solubilized calcium ions relative to the solubilized calcium ions naturally generated on dissolution of precipitated calcium carbonate by $H_3O^+$ ions, where said $H_3O^+$ ions are provided solely in the form of a counter ion to the anion, i.e. via the addition of the anion in the form of an acid or non-calcium acid salt, and in absence of any further calcium ion or calcium ion generating source.

Said excess solubilized calcium ions are preferably provided by the addition of a soluble neutral or acid calcium salt, or by the addition of an acid or a neutral or acid non-calcium salt which generates a soluble neutral or acid calcium salt in situ.

Said $H_3O^+$ ions may be provided by the addition of an acid or an acid salt of said anion, or the addition of an acid or an acid salt which simultaneously serves to provide all or part of said excess solubilized calcium ions.

In a further preferred embodiment of the preparation of the surface-reacted natural or precipitated calcium carbonate, the natural or precipitated calcium carbonate is reacted with the acid and/or the carbon dioxide in the presence of at least one compound selected from the group consisting of silicate, silica, aluminium hydroxide, earth alkali aluminate such as sodium or potassium aluminate, magnesium oxide, aluminium sulphate or mixtures thereof. Preferably, the at least one silicate is selected from an aluminium silicate, a calcium silicate, or an earth alkali metal silicate.

In another preferred embodiment, said at least one compound is aluminium sulphate hexadecahydrate. In a particularly preferred embodiment, said at least one compound is aluminium sulphate hexadecahydrate, wherein the at least one $H_3O^+$ ion donor is selected from the group consisting of hydrochloric acid, sulphuric acid, sulphurous acid, phosphoric acid, citric acid, oxalic acid, acetic acid, formic acid and mixtures thereof, more preferably the molar ratio of said $H3O+$ ion donor to the natural or precipitated calcium carbonate is from 0.01:1 to 4:1, more preferably from 0.02:1 to 2:1, even more preferably from 0.05:1 to 1:1 and most preferably from 0.1:1 to 0.58:1.

The foregoing components can be added to an aqueous suspension comprising the natural or precipitated calcium carbonate before adding the acid and/or carbon dioxide.

Alternatively, the foregoing components can be added to the aqueous suspension of natural or precipitated calcium carbonate while the reaction of natural or precipitated calcium carbonate with an acid and carbon dioxide has already started. Further details about the preparation of the surface-reacted natural or precipitated calcium carbonate in the presence of at least one silicate and/or silica and/or aluminium hydroxide and/or earth alkali aluminate component(s) are disclosed in WO2004083316 A1, the content of this reference herewith being included in the present document.

The surface-reacted calcium carbonate can be kept in suspension, optionally further stabilized by a dispersant. Conventional dispersants known to the skilled person can be used. A preferred dispersant is comprised of polyacrylic acids and/or carboxymethylcelluloses.

Alternatively, the aqueous suspension described above can be dried, thereby obtaining the solid (i.e. dry or containing as little water that it is not in a fluid form) surface-reacted natural or precipitated calcium carbonate in the form of granules or a powder.

In a preferred embodiment, the surface-reacted calcium carbonate has a specific surface area of from 10 to 200 m2/g, preferably from 20 to 180 m2/g, more preferably from 25 $m^2/g$ to 160 $m^2/g$, and most preferably from 30 to 140 m2/g, measured using nitrogen and the BET method according to ISO 9277:2010.

Additionally or alternatively, the surface-reacted calcium carbonate particles have a volume median particle size d50(vol) of from 0.1 to 90 µm, preferably from 0.1 to 75 µm, more preferably from 0.5 to 50 µm, even more preferably from 1 to 40 µm, and most preferably from 1.5 to 15 µm.

Additionally or alternatively, the surface-reacted calcium carbonate particles have a solid top cut particle size d98(vol) of ≤100 µm, preferably ≤60 µm, more preferably ≤45 µm, and most preferably ≤20 µm.

According to one embodiment of the present invention, the at least one mineral material is surface reacted calcium carbonate and has a) a volume median particle size (150 from 0.1 to 90 µm, preferably from 0.1 to 75 µm, more preferably from 0.5 to 50 µm, even more preferably from 1 to 40 µm and most preferably from 1.5 to 15 µm or b) a volume top cut ($d_{98}$) of ≤100 µm, preferably ≤60 µm, more preferably ≤45 µm and most preferably ≤20 µm, or c) a specific surface area (BET) of from 10 to 200 $m^2/g$, preferably from 20 to 180 $m^2/g$, even more preferably from 25 to 160 $m^2/g$ and most preferably from 30 to 140 $m^2/g$, measured using nitrogen and the BET method according to ISO 9277:2010.

According to another embodiment of the present invention, the at least one mineral material is surface reacted calcium carbonate and has a) a volume median particle size (150 from 0.1 to 90 µm, preferably from 0.1 to 75 µm, more preferably from 0.5 to 50 µm, even more preferably from 1 to 40 µm and most preferably from 1.5 to 15 µm and b) a volume top cut ($d_{98}$) of ≤100 µm, preferably ≤60 µm, more preferably ≤45 µm and most preferably ≤20 µm, and c) a specific surface area (BET) of from 10 to 200 $m^2/g$, preferably from 20 to 180 $m^2/g$, even more preferably from 25 to 160 $m^2/g$ and most preferably from 30 to 140 $m^2/g$, measured using nitrogen and the BET method according to ISO 9277:2010.

According to another embodiment, the surface-reacted calcium carbonate has an intra-particle intruded specific pore volume in the range from 0.1 to 2.3 cm3/g, more preferably from 0.2 to 2.0 cm3/g, especially preferably from 0.4 to 1.8 cm3/g and most preferably from 0.6 to 1.6 cm3/g, calculated from mercury porosimetry measurement.

The intra-particle pore size of the surface-reacted calcium carbonate preferably is in a range of from 0.004 to 1.6 µm, more preferably in a range of between 0.005 to 1.3 µm, especially preferably from 0.006 to 1.15 µm and most preferably of 0.007 to 1.0 µm, e.g., 0.004 to 0.50 µm determined by mercury porosimetry measurement.

The specific pore volume is measured using a mercury intrusion porosimetry measurement using a Micromeritics Autopore V 9620 mercury porosimeter having a maximum applied pressure of mercury 414 MPa (60 000 psi), equivalent to a Laplace throat diameter of 0.004 µm (~ nm). The equilibration time used at each pressure step is 20 seconds. The sample material is sealed in a 5 cm3 chamber powder penetrometer for analysis. The data are corrected for mercury compression, penetrometer expansion and sample material compression using the software Pore-Comp (Gane, P. A. C., Kettle, J. P., Matthews, G. P. and Ridgway, C. J., "Void Space Structure of Compressible Polymer Spheres and Consolidated Calcium Carbonate Paper-Coating Formulations", Industrial and Engineering Chemistry Research, 35(5), 1996, p 1753-1764.).

The total pore volume seen in the cumulative intrusion data can be separated into two regions with the intrusion data from 214 µm down to about 1-4 µm showing the coarse packing of the sample between any agglomerate structures contributing strongly. Below these diameters lies the fine interparticle packing of the particles themselves. If they also have intraparticle pores, then this region appears bi modal, and by taking the specific pore volume intruded by mercury into pores finer than the modal turning point, i.e. finer than the bi-modal point of inflection, the specific intraparticle pore volume is defined. The sum of these three regions gives the total overall pore volume of the powder, but depends strongly on the original sample compaction/settling of the powder at the coarse pore end of the distribution.

By taking the first derivative of the cumulative intrusion curve the pore size distributions based on equivalent Laplace diameter, inevitably including pore-shielding, are revealed. The differential curves clearly show the coarse agglomerate pore structure region, the interparticle pore region and the intraparticle pore region, if present. Knowing the intraparticle pore diameter range it is possible to subtract the remainder interparticle and interagglomerate pore volume from the total pore volume to deliver the desired pore volume of the internal pores alone in terms of the pore volume per unit mass (specific pore volume). The same principle of subtraction, of course, applies for isolating any of the other pore size regions of interest.

For the purpose of the present invention, the surface-reacted calcium carbonate is provided in dry form, which means that the at least one surface-reacted calcium carbonate according to the present invention has a residual total moisture content of less than 5 wt.-%, preferably less than 4 wt.-%, more preferably less than 3 wt.-%, even more preferably less than 2 wt.-% and most preferably less than 1 wt.-%, based on the total dry weight of the at least one surface-reacted calcium carbonate.

Alternatively, the at least one surface-reacted calcium carbonate according to one embodiment may have a residual total moisture content of from 0.01 to 1 wt.-%, preferably from 0.02 to 0.5 wt.-%, more preferably from 0.03 to 0.3 wt.-%, even more preferably from 0.04 to 0.2 wt.-% and most preferably from 0.05 to 0.15 wt.-%, based on the total dry weight of the at least one surface-reacted calcium carbonate.

According to another preferred embodiment the first filler comprises, preferably consist of hydromagnesite.

Hydromagnesite or basic magnesium carbonate, which is the standard industrial name for hydromagnesite, is a naturally occurring mineral which is found in magnesium rich minerals such as serpentine and altered magnesium rich igneous rocks, but also as an alteration product of brucite in periclase marbles. Hydromagnesite is described as having the following formula $Mg_5(CO_3)_4(OH)_2 \cdot 4H_2O$.

It should be appreciated that hydromagnesite is a very specific mineral form of magnesium carbonate and occurs naturally as small needle-like crystals or crusts of acicular or bladed crystals. In addition thereto, it should be noted that hydromagnesite is a distinct and unique form of magnesium carbonate and is chemically, physically and structurally different from other forms of magnesium carbonate. Hydromagnesite can readily be distinguished from other magnesium carbonates by X-ray diffraction analysis, thermogravimetric analysis or elemental analysis. Unless specifically described as hydromagnesite, all other forms of magnesium carbonates (e.g. artinite ($Mg_2(CO_3)(OH)_2 \cdot 3H_2O$), dypingite ($Mg_5(CO_3)_4(OH)_2 \cdot 5H_2O$), giorgiosite ($Mg_5(CO_3)_4(OH)_2 \cdot 5H_2O$), pokrovskite ($Mg_2(CO_3)(OH)_2 \cdot 0.5H_2O$), magnesite ($MgCO_3$), barringtonite ($MgCO_3 \cdot 2H_2O$), lansfordite ($MgCO_3 \cdot 5H_2O$) and nesquehonite ($MgCO_3 \cdot 3H_2O$)) are not hydromagnesite within the meaning of the present invention and do not correspond chemically to the formula described above.

Besides the natural hydromagnesite, synthetic hydromagnesites (or precipitated magnesium carbonates) can be prepared. For instance, U.S. Pat. No. 1,361,324, US935418, GB548197 and GB544907 generally describe the formation of aqueous solutions of magnesium bicarbonate (typically described as "$Mg(HCO_3)_2$"), which is then transformed by the action of a base, e.g., magnesium hydroxide, to form hydromagnesite. Other processes described in the art suggest to prepare compositions containing both, hydromagnesite and magnesium hydroxide, wherein magnesium hydroxide is mixed with water to form a suspension which is further contacted with carbon dioxide and an aqueous basic solution to form the corresponding mixture; cf. for example U.S. Pat. No. 5,979,461.

It is appreciated that the hydromagnesite can be one or a mixture of different kinds of hydromagnesite(s). In one embodiment of the present invention, the hydromagnesite comprises, preferably consists of, one kind of hydromagnesite. Alternatively, the hydromagnesite comprises, preferably consists of, two or more kinds of hydromagnesites. For example, the hydromagnesite comprises, preferably consists of, two or three kinds of hydromagnesites. Preferably, the hydromagnesite comprises, more preferably consists of, one kind of hydromagnesite.

In a preferred embodiment the at least one hydromagnesite has a volume median particle size d50 from 1 to 75 μm, preferably from 1.2 to 50 μm, more preferably from 1.5 to 30 μm, even more preferably from 1.7 to 15 μm and most preferably from 1.9 to 10 μm.

Additionally or alternatively, the at least one hydromagnesite has a volume top cut (d98) of ≤100 μm, preferably ≤60 μm, more preferably ≤45 μm and most preferably ≤20 μm.

Additionally or alternatively, the at least one hydromagnesite has a specific surface area (BET) of from 25 to 200 m2/g, preferably from 30 to 150 m2/g, even more preferably from 32 to 120 m2/g and most preferably from 35 to 100 m2/g, measured using nitrogen and the BET method according to ISO 9277:2010.

According to one embodiment of the present invention, the at least one mineral material is hydromagnesite and has
a) a volume median particle size d50 from 1 to 75 μm, preferably from 1.2 to 50 μm, more preferably from 1.5 to 30 μm, even more preferably from 1.7 to 15 μm and most preferably from 1.9 to 10 μm and
b) a volume top cut ($d_{98}$) of ≤100 μm, preferably ≤60 μm, more preferably ≤45 μm and most preferably ≤20 μm, and
c) a specific surface area (BET) of from 25 to 200 $m^2/g$, preferably from 30 to 150 $m^2/g$, even more preferably from 32 to 120 $m^2/g$ and most preferably from 35 to 100 $m^2/g$, measured using nitrogen and the BET method according to ISO 9277:2010.

According to another embodiment of the present invention, the at least one mineral material is hydromagnesite and has
a) a volume median particle size (150 from 1 to 75 μm, preferably from 1.2 to 50 μm, more preferably from 1.5 to 30 μm, even more preferably from 1.7 to 15 μm and most preferably from 1.9 to 10 μm or
b) a volume top cut (d9s) of ≤100 μm, preferably ≤60 μm, more preferably ≤45 μm and most preferably ≤20 μm, or
c) a specific surface area (BET) of from 25 to 200 $m^2/g$, preferably from 30 to 150 $m^2/g$, even more preferably from 32 to 120 $m^2/g$ and most preferably from 35 to 100 $m^2/g$, measured using nitrogen and the BET method according to ISO 9277:2010.

According to a preferred embodiment of the present invention the mineral material is a surface reacted calcium carbonate. Preferably the surface reacted calcium carbonate has a volume median particle size $d_{50}$ from 0.1 to 90 μm, preferably from 0.1 to 75 μm, more preferably from 0.5 to 50 μm, even more preferably from 1 to 40 μm and most preferably from 1.5 to 15 μm and a specific surface area (BET) of from 10 to 200 $m^2/g$, preferably from 20 to 180 $m^2/g$, even more preferably from 25 to 160 $m^2/g$ and most preferably from 30 to 140 $m^2/g$, measured using nitrogen and the BET method according to ISO 9277:2010. According to an exemplified embodiment of the present invention, the mineral material is surface reacted calcium carbonate that has a volume median particle size $d_{50}$ from 1.5 to 15 μm and a specific surface area (BET) of from 30 to 140 $m^2/g$, measured using nitrogen and the BET method according to ISO 9277:2010.

According to another preferred embodiment of the present invention the mineral material is hydromagnesite. Preferably the hydromagnesite has a volume median particle size $d_{50}$ from 1 to 75 μm, preferably from 1.2 to 50 μm, more preferably from 1.5 to 30 μm, even more preferably from 1.7 to 15 μm and most preferably from 1.9 to 10 μm and a specific surface area (BET) of from 25 to 200 $m^2/g$, preferably from 30 to 150 $m^2/g$, even more preferably from 32 to 120 $m^2/g$ and most preferably from 35 to 100 $m^2/g$, measured using nitrogen and the BET method according to ISO 9277:2010. According to an exemplified embodiment of the present invention, the mineral material is hydromagnesite that has a volume median particle size $d_{50}$ from 1.9 to 10 μm and a specific surface area (BET) of from 35 to 100 $m^2/g$, measured using nitrogen and the BET method according to ISO 9277:2010.

The at Least One Lignin

According to the present invention at least one lignin is present in the composition in an amount from 0.1 wt.-% to 100 wt.-%, based on the dry weight of the at least one mineral material of step a).

The term "at least one" lignin in the meaning of the present invention means that the lignin comprises, preferably consists of, one or more lignin(s).

In one embodiment of the present invention, the at least one lignin in the composition comprises, preferably consists of, one lignin. Alternatively, the at least one lignin comprises, preferably consists of, two or more lignins. For example, the at least one lignin comprises, preferably consists of, two or three lignins.

Preferably, the at least one lignin in the composition comprises, more preferably consists of, one lignin.

A "lignin" in the meaning of the present invention is defined as an organic biopolymer which is obtained from woods and plants. It is a cross-linked polymer with molecular masses in excess of 10000 u. Lignin is hydrophobic and rich in aromatic subunits and mainly comprises a cross-linked network 4-hydroxy-3-methoxyphenylpropane, 3,5-dimethoxy-4-hydroxyphenylpropane, and 4-hydroxyphenylpropane.

Lignin is known to the skilled person and commercially available, for example from Domsjö under the trade name Domsjö Lignin DS10.

Plant lignins can be broadly divided into three classes: softwood (gymnosperm), hardwood (angiosperm) and grass or annual plant (graminaceous) lignin. Three different phenylpropane units, or monolignols, are responsible for lignin biosynthesis. Guaiacyl lignin is composed principally of coniferyl alcohol units, while guaiacyl-syringyl lignin contains monomeric units from coniferyl and sinapyl alcohol. In general, guaiacyl lignin is found in softwoods while guaiacyl-syringyl lignin is present in hardwoods. Graminaceous lignin is composed mainly of p-coumaryl alcohol units. Lignin polymerization is initiated by oxidation of the phenylpropane phenolic hydroxyl groups. Stabilization of the radical occurs by coupling to another radical in any of the positions of the unpaired electron.

According to one embodiment of the present invention, the at least one lignin is a water soluble or water insoluble lignin selected from the group consisting of natural lignin, klason lignin, hydrolyzed lignin, milled wood lignin, soda lignin, organosolv lignin, kraft lignin, sulphonated lignin and mixtures thereof.

Natural lignin is the lignin that is present in plant tissues and is also known as native lignin.

Klason lignin is the acid insoluble lignin content in natural lignin. It is obtained by pre-hydrolysis of natural lignin in H2SO4, hydrolyzing the mixture at high temperatures and filtration. The retentate comprises the klason lignin. The Klason process is known to the skilled person.

Hydrolyzed lignin is obtained by refluxing lignin or lignocellulose with HCl in a dioxane/water composition. The treatment results in the degradation of lignin with formation of substantial amounts of arylpropanes and the majority of the acidolysis monomers originate from arylglycerol β-aryl ether structure.

Milled wood lignin (MWL) also known as Björkman lignin is obtained by grinding wood meal in a ball mill either dry or in the presence of nonswelling solvents such as, for example, toluene, wherein the cell structure of the wood is destroyed. A portion of lignin can be obtained from the suspension by extraction with a dioxane-water mixture. The Bjorkman process is known to the skilled person.

Kraft lignin also known as alkali lignin is the lignin obtained from the Kraft process also known as kraft pulping or sulfate process. The process is for the conversion of wood into wood pulp, which consists of almost pure cellulose fibers, the main component of paper and is known to the skilled person. The Kraft process entails treatment of wood chips with a hot mixture of water, sodium hydroxide (NaOH), and sodium sulfide (Na2S), known as white liquor, that breaks the bonds that link lignin, hemicellulose, and cellulose. The technology entails several steps, both mechanical and chemical.

Lignosulfonate also known as sulphonated lignin are water-soluble anionic polyelectrolyte polymers. They are obtained from wood by treating wood at elevated temperatures with solutions containing sulfur dioxide and hydrogen sulfite ions. This process is also known to the skilled person.

Soda lignin is obtained from the soda process which involves heating fibrous wood material in a pressurized reactor at high temperature in the presence of sodium hydroxide (i.e. soda), also known as cooking liquor. In the process, lignin is separating from the cellulose, and is suspended in the liquid phase, which is called black liquor. The black liquor therefore contains lignin and sodium hydroxide (soda) and is known as soda lignin.

Organosolv lignin is obtained by the organosolv process. The organosolv process includes extracting lignin from lignocellulosic biomass using organic solvents typically with an acidic catalyst. Organosolv lignin does not comprise sulfur or sulfonate groups and has a molecular weight of about 1000 to 2000 g/mole.

According to one embodiment of the present invention the at least one lignin is a mixture of two or more lignins e.g. is a mixture of two lignins, for example, sulphonated lignin and a further lignin, for example, kraft lignin or natural lignin.

According to a preferred embodiment of the present invention, the at least one lignin consist only of one lignin, preferably selected from natural lignin, klason lignin, hydrolyzed lignin, milled wood lignin, soda lignin, organosolv lignin, kraft lignin, or sulphonated lignin and most preferably consist merely of kraft lignin.

According to one embodiment of the present invention the at least one lignin is water soluble lignin. According to another embodiment of the present invention the at least one lignin is water insoluble lignin. Preferably, the at least one lignin is water insoluble lignin and most preferably the at least one water insoluble lignin is selected from the group consisting of klason lignin, kraft lignin and mixtures thereof and most preferably is kraft lignin.

According to another embodiment of the present invention the at least one lignin has a molecular mass above 10000 u, preferably between 15000 and 1000000 u even more preferably between 50000 to 800000 u and most preferably between 100000 and 500000 u.

The at least one lignin is present in the composition in an amount from 0.1 to 100 wt.-% based on the dry weight of the at least one mineral material of step a). According to a preferred embodiment of the present invention, the at least one lignin is present in the composition in an amount from 1 to 80 wt.-% based on the dry weight of the at least one mineral material of step a), preferably in an amount of 2 to 50 wt.-%, even more preferably in an amount of 3 to 30 wt.-%, and most preferably in an amount of 5 to 25 wt.-%.

The Dry Composition

The inventive dry composition for chemical and physical sun protection comprises a) at least one mineral material selected from the group consisting of surface reacted calcium carbonate and/or hydromagnesite, wherein the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source and b) from 0.1 wt.-% to 100 wt.-%, based on the dry weight of the at least one mineral material of step a) of at least one lignin.

Alternatively, the inventive dry composition for chemical and physical sun protection consists of a) at least one mineral material selected from the group consisting of surface reacted calcium carbonate and/or hydromagnesite, wherein the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source and b) from 0.1 wt.-% to 100 wt.-%, based on the dry weight of the at least one mineral material of step a) of at least one lignin.

Preferably, the inventive dry composition for chemical and physical sun protection comprises a) at least one mineral material selected from the group consisting of surface reacted calcium carbonate and/or hydromagnesite, wherein the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source and b) from 0.1 wt.-% to 100 wt.-%, based on the dry weight of the at least one mineral material of step a) of at least one lignin. In that case other compounds may be present in the composition.

According to one embodiment of the present invention, the composition further comprises an organic solvent.

An "organic solvent" in the meaning of the present invention is a compound that is liquid at room temperature and that is different from water. Room temperature refers to a temperature of 25° C. Preferably the organic solvent is able to dissolve at least one lignin and preferably a non-water soluble lignin.

The organic solvent of the present invention can be any organic solvent that is suitable for the inventive composition. The skilled person knows how to select such an organic solvent. Organic solvents are known to the skilled person and are commercially available.

According to one embodiment of the present invention, the organic solvent is selected from the group consisting of hexane, toluene, methanol, ethanol, dioxane, acetone, dimethyl sulfoxide, dimethylformamide, ethylene glycol, ethylacetate, glycerol, γ-valerolactone, polyethylene glycol, polypropylene glycol and mixtures thereof, more preferably is selected from the group consisting of ethylene glycol, ethylacetate, glycerol, γ-valerolactone, polyethylene glycol, polypropylene glycol and mixtures thereof, and most preferably is γ-valerolactone.

Hexane is an alkane of six carbon atoms, with the chemical formula $C_6H_{14}$ and comprises five structural isomers. All hexanes are colorless liquids, odorless when pure, with boiling points between 50 and 70° C.

Toluene is an aromatic hydrocarbon with the formula $C_6H_5CH_3$ and is a colorless, water-insoluble liquid with the smell associated with paint thinners.

Methanol, also known as methyl alcohol among others, is a chemical with the formula $CH_3OH$. Ethanol, also known as ethyl alcohol among others, is a chemical with the formula $CH_3-CH_2-OH$.

Dioxane is a heterocyclic organic compound, classified as an ether. It is a colorless liquid with a faint sweet odor. Dioxane comprises the isomers 1,2-dioxane, 1,3-dioxane and 1,4-dioxane.

Acetone, or propanone, is the organic compound with the formula $(CH_3)_2CO$. It is a colorless, volatile, flammable liquid and is the simplest and smallest ketone.

Dimethyl sulfoxide (DMSO) is an organosulfur compound with the formula $(CH_3)_2SO$. This colorless liquid is a polar aprotic solvent that dissolves both polar and nonpolar compounds and is miscible in a wide range of organic solvents as well as water.

Dimethylformamide is an organic compound with the formula $(CH_3)_2NC(O)H$. Commonly abbreviated as DMF, this colorless liquid is miscible with water and the majority of organic liquids.

Ethylene glycol also known as ethane-1,2-diol is an organic compound with the chemical formula $(CH_2OH)_2$. It is an odorless, colorless, sweet-tasting, viscous liquid.

Ethyl acetate is an organic compound with the formula $CH_3-COO-CH_2-CH_3$. It is a colorless liquid and has a characteristic sweet smell. Ethyl acetate is the ester of ethanol and acetic acid.

Glycerol is also called glycerine or glycerin or propane-1,2,3-triol and is a simple polyol compound. It is a colorless, odorless, viscous liquid that is sweet-tasting and non-toxic. It has the chemical formula $CH_2OH-CHOH-CH_2OH$.

γ-valerolactone is an organic compound with the formula $C_5H_8O_2$. This colorless liquid is chiral but is usually used as the racemate. It is readily obtained from cellulosic biomass and is a potential fuel and green solvent.

Polyethylene glycol is a polyether compound with many applications, from industrial manufacturing to medicine. PEG is also known as polyethylene oxide (PEO) or polyoxyethylene (POE), depending on its molecular weight. The structure of PEG is commonly expressed as $H-(O-CH_2-CH_2)_n-OH$.

Polypropylene glycol or polypropylene oxide is the polymer of propylene glycol. Chemically it is a polyether. The structure of PPG is commonly expressed as $H-(O-CHCH_3-CH_2)_n-OH$.

According to a preferred embodiment of the present invention the solvent is γ-valerolactone.

According to one embodiment of the present invention the organic solvent is present in the composition in an amount of 0.1 to 200 wt.-%, based on the dry weight of the at least one mineral material of step a), more preferably in an amount of 0.5 to 100 wt.-%, even more preferably in an amount of 0.75 to 50 wt.-% and most preferably in an amount of 1 to 25 wt.-%.

Additionally or alternatively, the organic solvent is present in the composition in an amount of 100 to 500 wt.-%, based on the dry weight of the at least one lignin of step b), more preferably in an amount of 150 to 450 wt.-% and most preferably in an amount of 200 to 300 wt.-%.

According to one embodiment of the present invention the organic solvent is present in the composition in an amount of 0.1 to 200 wt.-%, based on the dry weight of the at least one mineral material of step a), preferably in an amount of 0.5 to 100 wt.-%, more preferably in an amount of 0.75 to 50 wt.-% and most preferably in an amount of 1 to 25 wt.-% or in an amount of 100 to 500 wt.-%, based on the dry weight of the at least one lignin of step b), more preferably in an amount of 150 to 450 wt.-% and most preferably in an amount of 200 to 300 wt.-%.

According to another embodiment of the present invention the organic solvent is present in the composition in an amount of 0.1 to 200 wt.-%, based on the dry weight of the at least one mineral material of step a), preferably in an amount of 0.5 to 100 wt.-%, more preferably in an amount of 0.75 to 50 wt.-% and most preferably in an amount of 1 to 25 wt.-% and in an amount of 100 to 500 wt.-%, based on the dry weight of the at least one lignin of step b), more preferably in an amount of 150 to 450 wt.-% and most preferably in an amount of 200 to 300 wt.-%.

According to one embodiment of the present invention the dry composition comprises a) at least one mineral material selected from the group consisting of surface reacted calcium carbonate and/or hydromagnesite, wherein the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source and b) from 0.1 wt.-% to 100 wt.-%, based on the dry weight of the at least one mineral material of step a) of at least one lignin and c) an organic solvent.

According to another embodiment of the present invention the dry composition consist of a) at least one mineral material selected from the group consisting of surface reacted calcium carbonate and/or hydromagnesite, wherein the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source and b) from 0.1 wt.-% to 100 wt.-%, based on the dry weight of the at least one mineral material of step a) of at least one lignin and c) an organic solvent.

The organic solvent may further comprise water or may be used in combination with water. However, the amount of water in the organic solvent or when used in combination with the organic solvent is rather low. More precisely, even if water is present in the organic solvent or is used in combination with the organic solvent still a dry composition according to the present invention is obtained.

As already set out above, a "dry" composition, is understood to be a composition having less than 5.0% by weight of water relative to the composition weight. Preferably, the dry composition according to the present invention comprises less than 4 wt.-%, more preferably less than 3 wt.-%, even more preferably less than 2 wt.-% and most preferably less than 1 wt.-% water, based on the total dry weight of the composition.

According to another embodiment of the present invention, the composition further comprises at least one inorganic UV filter. The term "inorganic UV filter" as used herein refers to an inorganic particulate material, which can reflect, scatter and/or absorb ultraviolet (UV) radiation in the UV-A and/or UV-B region of the electromagnetic spectrum, i.e. electromagnetic radiation having a wavelength between 280 and 400 nm. The at least one inorganic UV filter is selected from the group consisting of titanium dioxide, zinc oxide, iron oxide, cerium oxide, calcium-doped cerium oxide, cerium phosphate, and mixtures thereof, preferably the least one inorganic UV filter is selected from the group consisting of titanium dioxide, zinc oxide, and mixtures thereof, more preferably the at least one inorganic UV filter is titanium dioxide and/or zinc oxide, and most preferably the at least one inorganic UV filter is titanium dioxide.

The at least one inorganic UV filter may be present in form of particles. For example, the at least one inorganic UV filter is in form of particles having a weight median particle size d50 from 10 to 1000 nm, preferably from 12 to 800 nm, more preferably from 15 to 600 nm, and most preferably from 20 to 400 nm. The surface of said particles can be uncoated or can be at least partially coated, for example, in order to improve their dispersibility or to prevent any potential photocatalytic activity of said materials. Examples of suitable surface coating materials are silica, hydrated silica, alumina, aluminium hydroxide, aluminium stearate, stearic acid, trimethoxycaprylsilane, glycerine, dimethicone, hydrogen dimethicone, simeticone, and mixtures thereof. However, any other suitable coating material known the skilled person may be used.

It is appreciated that the dry composition may comprise the at least one inorganic UV filter and its amount in dependence of the dry composition to be prepared and/or the manufacturer's needs.

For example, the at least one inorganic UV filter may be present in an amount from 1 to 50 wt.-%, based on the total weight of the dry composition, preferably from 2 to 40 wt.-%, more preferably from 5 to 30 wt.-%, and most preferably from 10 to 25 wt.-%, e.g. from 10 to 20 wt.-%.

According to another embodiment of the present invention, the composition further comprises at least one organic UV filter. Preferably, the at least one organic UV filter is selected from the group consisting of derivatives of cinnamic acid and its salts, derivatives of salicylic acid and its salts, benzophenones, derivatives of aminobenzoic acid and its salts, dibenzoylmethanes, benzylidenecamphor derivatives, benzimidazole derivatives, diphenylacrylate derivatives, acrylamide derivatives, benzotriazole derivatives, triazine derivatives, benzalmalonate derivatives, aminobenzoate derivatives, octocrylene, and mixtures thereof, preferably derivatives of cinnamic acid and its salts, benzophenones, octocrylene, and mixtures thereof.

It is appreciated that the dry composition may comprise the at least one organic UV filter and its amount in dependence of the dry composition to be prepared and/or the manufacturer's needs.

For example, the at least one organic UV filter may be present in an amount from 1 to 50 wt.-%, based on the total weight of the dry composition, preferably from 0.5 to 20 wt.-%, more preferably from 1 to 15 wt.-%, and most preferably from 2 to 12 wt.-%, e.g. from 3 to 10 wt.-%.

The term "organic UV filter" as used herein refers to an organic material, which can absorb ultraviolet (UV) radiation in the UV-A and/or UV-B region of the electromagnetic spectrum, i.e. electromagnetic radiation having a wavelength between 280 and 400 nm.

According to one embodiment of the present invention, the composition further comprises at least one salt. A "salt" in the meaning of the present invention refers to a chemical compound consisting of an ionic assembly of cations and anions and is composed of related numbers of cations (positively charged ions) and anions (negatively charged ions) so that the product is electrically neutral (without a net charge). According to a preferred embodiment, the at least one salt comprises carbonate ions. According to another preferred embodiment, the at least one salt comprises sodium, ammonium, calcium and/or magnesium cations.

Preferably the at least one salt comprises ammonium carbonate, sodium carbonate, calcium salts, magnesium salts or mixtures thereof. The salts can be formed during the preparation of the dry composition for chemical and physical sun protection. More precisely, the salts may be formed from a reaction between the at least one aqueous solution having a pH≥10 and the at least one mineral material selected from the group consisting of surface reacted calcium carbonate and/or hydromagnesite. Dependent on the at least mineral material and the base present in the aqueous solution, different salts may form during the reaction.

According to one embodiment of the present invention, the at least one lignin is present in the composition in form of a mixture with the at least one mineral material. In that case the at least one lignin and the at least one mineral material coexist in the inventive composition.

According to another embodiment of the present invention, the at least one lignin is present in the composition in the form of a coating on the at least one mineral material. In that case the at least one lignin is located on the surface of the at least one mineral material.

According to a preferred embodiment of the present invention the at least one lignin is present in the composition in the form of a coating on the at least one mineral material. Preferably, the at least one lignin in the coating on the at least one mineral material is a water insoluble lignin, and preferably kraft lignin.

The skilled person knows how to prepare coated particles. Preferably these coated particles are prepared by mixing the components of the inventive composition in the presence of an organic solvent and afterwards drying the mixture.

Mixing may be done consecutively in any order or simultaneously. For example, the at least one lignin may be solved in the organic solvent and afterwards, the at least one mineral material may be added. Alternatively, the at least one mineral material may be dispersed in the organic solvent and afterwards, the at least one lignin may be added. According to another embodiment all the compounds may be mixed simultaneously.

The mixing may be carried out under conventional mixing conditions and with conventional mixing apparatuses such as Lödige mixers etc. The skilled person will adapt these mixing conditions (such as the configuration of mixing pallets and mixing speed) according to his process equipment. It is appreciated that any mixing method which would be suitable may be used.

In one embodiment, mixing is carried out at a temperature in the range from 15 to 120° C., more preferably from 20 to 110° C. and most preferably from 30 to 100° C. Mixing can be performed for at least 1 s, at least 10 s, at least 30 s, at least 1 min, at least 10 min or at least 1 h.

The drying may be carried out in a single step such as spray drying, or in at least two steps, e.g. by applying a first heating step to the calcium carbonate in order to reduce the associated moisture content. The residual total moisture content may be further reduced by applying a second heating step to the calcium carbonate. In case said drying is carried out by more than one drying steps, the first step may be carried out by heating in a hot current of air, while the second and further drying steps are preferably carried out by an indirect heating.

The obtained at least one mineral material that is coated with the at least one lignin may be further deagglomerated, for example, during a grinding step. In general, the grinding step can be carried out with any conventional grinding device, for example, under conditions such that refinement predominantly results from impacts with a secondary body, i.e. in one or more of: a ball mill, a rod mill, a vibrating mill, a roll crusher, a centrifugal impact mill, a vertical bead mill an attrition mill, a pin mill, a hammer mill, a pulveriser, a shredder, a de-dumper, a knife cutter, or other such equipment known to the skilled man.

According to one embodiment of the present invention, the composition of the present invention is in solid form, preferably in form of a particulate material. The term "particulate" in the meaning of the present application refers to materials composed of a plurality of particles. Said plurality of particles may be defined, for example, by its particle size distribution. The expression "particulate material" may comprise powders, grains, tablets, flakes or crumbles.

According to a preferred embodiment of the present invention the dry composition comprises at least one mineral material selected from surface reacted calcium carbonate wherein the surface-reacted calcium carbonate is a reaction product of natural ground calcium carbonate or precipitated calcium carbonate with carbon dioxide and one or more H3O+ ion donors, wherein the carbon dioxide is formed in situ by the H3O+ ion donors treatment and/or is supplied from an external source and/or hydromagnesite, from 0.1 wt.-% to 100 wt.-%, based on the dry weight of the at least one mineral material of at least one lignin and an organic solvent. The lignin is a water soluble or water insoluble lignin selected from the group consisting of natural lignin, klason lignin, hydrolyzed lignin, milled wood lignin, soda lignin, organosolv lignin, kraft lignin, sulphonated lignin and mixtures thereof, preferably is a water-insoluble lignin selected from the group consisting of klason lignin, kraft lignin and mixtures thereof and most preferably is kraft lignin. The organic solvent is selected from the group consisting of hexane, toluene, methanol, ethanol, dioxane, acetone, dimethyl sulfoxide, dimethylformamide, ethylene glycol, ethylacetate, glycerol, γ-valerolactone, polyethylene glycol, polypropylene glycol and mixtures thereof, more preferably is selected from the group consisting of ethylene glycol, ethylacetate, glycerol, γ-valerolactone, polyethylene glycol, polypropylene glycol and mixtures thereof, and most preferably is γ-valerolactone. According to an exemplified embodiment of the present invention, the dry composition comprises at least one mineral material selected from surface reacted calcium carbonate wherein the surface-reacted calcium carbonate is a reaction product of natural ground calcium carbonate or precipitated calcium carbonate with carbon dioxide and one or more H3O+ ion donors, wherein the carbon dioxide is formed in situ by the H3O+ ion donors treatment and/or is supplied from an external source and/or hydromagnesite, from 0.1 wt.-% to 100 wt.-%, based on the dry weight of the at least one mineral material of at least one lignin, preferably kraft lignin and an organic solvent, preferably γ-valerolactone.

The Emulsion

The emulsion for chemical and physical sun protection of the present invention comprises a water in oil or oil in water mixture and 0.1 to 40 wt.-% of the dry composition according to the present invention, based on the weight of the water in oil or oil in water mixture.

The dry composition has already been described in detail above.

An emulsion in the meaning of the present invention is a mixture of two or more liquids that are normally immiscible and one liquid (the dispersed phase) is dispersed in the other (the continuous phase). An oil-in-water emulsion according to the present invention is an emulsion, wherein the oil is the dispersed phase, and water is the continuous phase. A water-in-oil emulsion according to the present invention is an emulsion, wherein water is the dispersed phase and oil is the continuous phase.

An oil in the meaning of the present invention is a liquid or solid silicon and/or hydrocarbon containing compound. The oil of the present invention can be any oil that is suitable for the inventive composition. The skilled person knows how to select such an oil. Oils are known to the skilled person and are commercially available.

Any oil known to the skilled person as being suitable in cosmetic formulations may be used. For example, the oil may be selected from the group comprising alkanecoconut-ester, polydimethylsiloxanes, polyalkylmethylsiloxanes, silicones, petroleum jelly such as vaseline, vegetable oils such as palm oil, esters of vegetable oils, and mixtures thereof. Preferably, the at least one oil is alkanecoconutester or vaseline.

The water of the present invention may be selected from drinking water, process water, demineralized water, distilled water, rain water, recycled water, river water and mixtures thereof. According to a preferred embodiment of the present invention the water present in the fluid composition is drinking water.

Drinking water, also known as potable water, is water that is safe to drink or to use for food preparations. Rain water/river water is obtained from rain/rivers. Recycled water is water that has been recycled and can be used in agriculture. Process water is water which is not considered drinkable and is basically used in relation to industrial plants, industrial processes and production facilities. Demin-eralized water is specially purified water that has had most or all of its mineral and salt ions removed, such as calcium, magnesium, sodium, chloride, sulphate, nitrate and bicar-bonate. It is also known as deionized water. Distilled water is water that has been boiled into vapor and condensed back into liquid in a separate container.

Preferably the emulsion according to the present inven-tion comprises water and oil in a ratio of water:oil from 100:0.1 to 100:100000, preferably from 100:1 to 100:10000, more preferably from 100:10 to 100:1000, even more pref-erably from 100:20 to 100:500 and most preferably from 100:25 to 100:400, based on the weight of the water and the dry oil.

The emulsion according to the present invention may comprise further compounds such as dispersing agents, emulsifiers, preservatives, active agents, cosmetic ingredi-ents, colored pigments, skin active substances etc.

According to one embodiment of the present invention, the emulsion merely consists of at least one mineral material according to the present invention, lignin and water in oil or oil in water mixture. According to another preferred embodi-ment of the present invention, the emulsion merely consists of at least one mineral material according to the present invention, lignin, an organic solvent and water in oil or oil in water mixture. According to another preferred embodi-ment of the present invention, the emulsion merely consists of at least one mineral material, lignin, an organic solvent, a skin active substance and water in oil or oil in water mixture.

According to one embodiment of the present invention the emulsion comprises water in oil or oil in water mixture and 0.1 to 40 wt.-% of the dry composition according to the present invention, based on the weight of the water in oil or oil in water mixture, preferably 0.25 to 20 wt.-%, even more preferably 0.5 to 10 wt.-% and most preferably 1 to 5 wt.-%.

Alternatively, the amount of the at least one mineral material and the at least one lignin is from 0.1 to 10 wt.-%, based on the total weight of the emulsion, preferably from 0.25 to 7 wt.-%, more preferably in an amount of 0.5 to 5 wt.-% and most preferably in an amount of 1 to 3 wt.-%.

The skilled person knows how to prepare such emulsions. Preferably, these emulsions are prepared by first preparing the water in oil or oil in water mixtures and afterwards mixing the dry composition according to the present inven-tion with these emulsions. Alternatively, these emulsions are prepared by mixing all the components and afterwards emulsifying these mixtures.

Mixing and emulsifying may be done consecutively in any order or simultaneously. For example, the dry compo-sition may be added to the water in oil or oil in water mixture in one or several portions. Alternatively, the at least one mineral material, the at least one lignin and the optional organic solvent may be added to the water in oil or oil in water mixture in any order. According to another embodi-ment all these compounds may be mixed simultaneously. Alternatively, the dry composition may be mixed with water and oil in any order or simultaneously in one or several portions and, afterwards, this mixture is emulsified.

The mixing and/or emulsifying may be carried out under conventional mixing and/or emulsifying conditions. The skilled person will adapt these mixing and/or emulsifying conditions (such as the configuration of mixing pallets and mixing speed) according to his process equipment. It is appreciated that any mixing and/or emulsifying method which would be suitable may be used.

In one embodiment, mixing and/or emulsifying is carried out at a temperature in the range from 15 to 100° C., more preferably from 20 to 95° C. and most preferably from 30 to 90° C. Mixing and/or emulsifying can be performed for at least 1 s, at least 10 s, at least 30 s, at least 1 min, at least 10 min or at least 1 h.

The inventors surprisingly found out that the foregoing composition/emulsion provides sufficient or improved chemical and physical sun protection. More precisely, the inventors surprisingly found out that the inventive compo-sition offers two different mechanisms for UV-B and/or UV-A protection to living cells, especially to human skin by different mechanisms, namely by reflecting the UV-B and/or UV-A radiation as well as by absorbing the UV-B and/or UV-A radiation.

UV-B and/or UV-A protection can be measured by trans-mittance, reflectance or absorption measurements. Ultravio-let-visible spectroscopy or ultraviolet-visible spectropho-tometry and Near Infrared spectroscopy (UV-Vis or UV/Vis and NIR) refers to a transmittance, reflectance or absorption spectroscopy in the ultraviolet-visible and near infrared spectral region. This means it uses light in the visible and adjacent ranges. The transmittance, reflectance or absorption in this range directly affects the perceived color of the chemicals involved. In this region of the electromagnetic spectrum, atoms and molecules undergo electronic transi-tions. As used herein, the reflectance is measured by a double beam PerkinElmer Lambda 950 UV/Vis/NIR spec-trometer equipped with a 150 mm integrating sphere with PMT and InGaAs detectors.

According to one embodiment of the present invention the composition/emulsion of the present invention has an improved UV-B and/or UV-A protection to living cells, especially to human skin, compared to an identical compo-sition/emulsion that comprises merely at least one mineral material or at least one lignin.

An "identical composition/identical emulsion" in the meaning of the present invention refers to a composition/ emulsion that consists of the same ingredients in the same amounts than the inventive composition/emulsion with the exception, that the composition does not comprise both of at least one mineral material and at least one lignin, but only mineral material or only lignin. The missing component is replaced by the other component.

According to another embodiment of the present invention the composition/emulsion of the present invention has an improved UV-B and/or UV-A protection to living cells, especially to human skin, compared to a composition/emulsion that comprises the same compounds but instead of at least one mineral material selected from the group consisting of surface reacted calcium carbonate and/or hydromagnesite, wherein the surface-reacted calcium carbonate is a reaction product of natural ground calcium carbonate or precipitated calcium carbonate with carbon dioxide and one or more H3O+ ion donors, wherein the carbon dioxide is formed in situ by the H3O+ ion donors treatment and/or is supplied from an external source, a different mineral material.

According to one preferred embodiment of the present invention the composition/emulsion of the present invention has an improved transmittance and reflectance in the range of 280 nm to 320 nm, compared to an identical composition/emulsion that comprises merely at least one mineral material, or alternatively in the range of >320 nm to 400 nm, and most preferably in the range of 280 nm to 400 nm.

Furthermore, the inventors surprisingly found that the composition/emulsion of the present invention can be easily and quickly produced, is cheap and especially easy to handle. More precisely, the composition/emulsion of the present invention can be easily produced by mixing and/or emulsifying the components of the inventive composition/emulsion as described above.

Furthermore, in case the at least one lignin is present in the composition/emulsion in the form of a coating on the at least one mineral material the inventors found out that these coated particles offer two different mechanisms for UV-B and/or UV-A protection to living cells, especially to human skin by different mechanisms, namely by reflecting the UV-B and/or UV-A radiation as well as by absorbing the UV-B and/or UV-A radiation.

Since the at least one mineral material and the lignin are non-toxic to humans and do not provide a harmful effect on the environment also these coated particles are non-toxic to humans and do not provide a harmful effect on the environment. These compounds are also often approved for use in cosmetic applications. Additionally, if the present compositions are used in combination with known inorganic or organic UV filters the amount of these UV filters can be reduced and the compositions still have the same or improved chemical and physical sun protection.

Furthermore, in case the at least one lignin in the coating on the at least one mineral material is a water insoluble lignin, for example kraft lignin, the inventors surprisingly found out that the coating sticks to the at least one mineral material even after redispersing the coated mineral material particles in water. Therefore, the coating layer is preserved even if the particles are dispersed in water. For example, if such a composition is incorporated in a cosmetic formulation on water basis, the lignin will not be washed away from the human skin by sweat easily since it sticks to the surface of the mineral material.

Furthermore, if the emulsions of the present invention having chemical and physical sun protection are used in cosmetic formulations these compositions might have improved appearance and/or sensory properties. Especially, these cosmetic formulations might show a reduced whitening effect when applied to the skin. Furthermore, these cosmetic formulations might be easily applied to the skin and form an even and uniform film on the skin. Moreover, such a cosmetic formulation might be less greasy and sticky, might exhibit a good spreadability and might dry fast.

Use of the Emulsion

The present invention refers to the use of an emulsion according to the present invention. More precisely, the present invention refers to the use of an emulsion comprising a water in oil or oil in water mixture and 1 to 40 wt.-% of the dry composition according to the present invention, based on the weight of the water in oil or oil in water mixture for chemical and physical sun protection in a cosmetic formulation.

This can be easily done by applying the inventive emulsion into a cosmetic formulation by any suitable method known to the skilled person, for example, by mixing, dispersing or emulsifying. According to a preferred method the ingredients of the cosmetic formulation are mixed with the inventive emulsion. Equipment therefore is known to the skilled person and commercially available.

According to one embodiment of the present invention, the cosmetic formulation is a sunscreen product, facial makeup product, hair care product, hand care product, skin care product, body care product and mixtures thereof.

According to another preferred embodiment the at least one lignin which is present in the cosmetic formulation in the form of a coating on the at least one mineral material. Additionally or alternatively, the at least one lignin in the cosmetic formulation is a water-insoluble lignin and preferably kraft lignin.

According to another preferred embodiment the at least one lignin which is present in the cosmetic formulation in the form of a coating on the at least one mineral material and the at least one lignin in the cosmetic formulation is a water-insoluble lignin and preferably kraft lignin.

According to another preferred embodiment the at least one lignin which is present in the cosmetic formulation in the form of a coating on the at least one mineral material or the at least one lignin in the cosmetic formulation is a water-insoluble lignin and preferably kraft lignin.

As already set out above the inventors surprisingly found out that the foregoing compositions provide sufficient sun protection to living cells and especially to human skin. The inventors surprisingly found that when an emulsion comprising a water in oil or oil in water mixture and 1 to 40 wt.-% of the dry composition according to the present invention, based on the weight of the water in oil or oil in water mixture is used, the composition provides improved sun protection, namely sun protection which includes physical as well as chemical protection to human skin.

Method for Preparing the Inventive Composition

The present invention refers to a method for preparing the inventive dry compositions for chemical and physical sun protection. The method comprises the steps of i) providing at least one organic solvent and/or at least one aqueous solution having a pH≥10, ii) providing at least one lignin, iii) providing at least one mineral material selected from the group consisting of surface reacted calcium carbonate and/or hydromagnesite, wherein the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source, iv) mixing, in any order, the at least one organic solvent and/or at least one aqueous solution of step i) with the lignin of step ii), to obtain a lignin solution, v) mixing, in any order, the lignin solution obtained in step iv) with the at least one mineral material of step iii) in an amount such that the amount of dry lignin is 0.1 wt.-% to 100 wt.-%, based on the dry weight of the at least one mineral material and vi) drying the suspension obtained in step v) to obtain the inventive dry composition.

The at least one lignin and the at least one mineral material have already been described in detail above.

According to step i) at least one organic solvent and/or at least one aqueous solution having a pH≥10 is provided.

An "organic solvent" in the meaning of the present invention is a compound that is liquid at room temperature and that is different from water. Room temperature refers to a temperature of 25° C. Preferably the organic solvent is able to dissolve the at least one lignin, preferably a non-water soluble lignin.

The organic solvent of the present invention can be any organic solvent that is suitable for the preparation of the inventive composition. The skilled person knows how to select such an organic solvent. Organic solvents are known to the skilled person and are commercially available.

According to one embodiment of the present invention, the organic solvent is selected from the group consisting of hexane, toluene, methanol, ethanol, dioxane, acetone, dimethyl sulfoxide, dimethylformamide, ethylene glycol, ethylacetate, glycerol, γ-valerolactone, polyethylene glycol, polypropylene glycol and mixtures thereof, more preferably is selected from the group consisting of ethylene glycol, ethylacetate, glycerol, γ-valerolactone, polyethylene glycol, polypropylene glycol and mixtures thereof, and most preferably is γ-valerolactone.

An "aqueous solution" in the meaning of the present invention is a compound that comprises water and is liquid at room temperature. Room temperature refers to a temperature of 25° C. Preferably the aqueous solution is able to dissolve the at least one lignin, preferably a water soluble lignin or water insoluble lignin. More precisely, the inventors surprisingly have found that it is possible to dissolve water insoluble lignins at pH values at pH 10 or higher.

According to one embodiment of the present invention, at least one organic solvent is provided in step i). Preferably the organic solvent is γ-valerolactone.

According to another embodiment of the present invention, at least one aqueous solution having a pH≥10 is provided in step i). Preferably the aqueous solution comprises caustic soda, ammonia solution, sodium hydroxide, potassium hydroxide, lye, sodium carbonate, calcium hydroxide, magnesium hydroxide and mixtures thereof and more preferably is ammonia solution.

Additionally, or alternatively, the aqueous solution has a pH between 10.5 and 13.5, even more preferably between 11.0 and 13.0 and most preferably between 11.5 and 12.5.

In step iv), the at least one organic solvent and/or at least one aqueous solution of step i) are mixed, in any order, with the lignin of step ii), to obtain a lignin solution.

Mixing may be done in any order. For example, the at least one lignin may be added to the at least one organic solvent and/or at least one aqueous solution having a pH≥10. Alternatively, the at least one organic solvent and/or at least one aqueous solution having a pH≥10 may be added to the at least one lignin. The addition may be done in one portion or in several portions, for example in two, three or five portions. If the addition is done in several portions, the portions may be equal or different. Preferably, they are equal.

According to a preferred embodiment, the at least one lignin may be added to the at least one organic solvent and/or at least one aqueous solution having a pH≥10 in one portion.

The mixing may be carried out under conventional mixing conditions and with conventional mixing apparatuses such as Lödige mixers, spray dryers etc. The skilled person will adapt these mixing conditions (such as the configuration of mixing pallets and mixing speed) according to his process equipment. It is appreciated that any mixing method which would be suitable may be used.

In one embodiment, mixing is carried out at a temperature in the range from 15 to 90° C., more preferably from 20 to 80° C. and most preferably from 30 to 70° C. Mixing can be performed for at least 1 s, at least 10 s, at least 30 s, at least 1 min, at least 10 min or at least 1 h.

In step v), the lignin solution obtained in step iv) is mixed with the at least one mineral material of step iii) in an amount such that the amount of dry lignin is 0.1 wt.-% to 100 wt.-%, based on the dry weight of the at least one mineral material.

Mixing may be done in any order. For example, the lignin solution obtained in step iv) may be added to the at least one mineral material of step iii). Alternatively, the at least one mineral material of step iii) may be added to the lignin solution obtained in step iv) The addition may be done in one portion or in several portions, for example in two, three or five portions. If the addition is done in several portions, the portions may be equal or different. Preferably, they are equal.

According to a preferred embodiment, the at least one mineral material of step iii) may be added to the lignin solution obtained in step iv) in one portion.

The lignin solution obtained in step iv) is mixed with the at least one mineral material of step iii) in an amount such that the amount of dry lignin is 0.1 wt.-% to 100 wt.-%, based on the dry weight of the at least one mineral material, preferably 1 to 80 wt.-%, more preferably 2 to 50 wt.-%, even more preferably 3 to 30 wt.-% and most preferably 5 to 25 wt.-%, based on the dry weight of the at least one mineral material.

The mixing may be carried out under conventional mixing conditions and with conventional mixing apparatuses such as Lödige mixers etc. The skilled person will adapt these mixing conditions (such as the configuration of mixing pallets and mixing speed) according to his process equipment. It is appreciated that any mixing method which would be suitable may be used.

According to a preferred embodiment of the present invention, the at least one mineral material may be dried before being mixed with the lignin solution obtained in step iv).

In one embodiment, mixing is carried out at a temperature in the range from 15 to 90° C., more preferably from 20 to 80° C. and most preferably from 30 to 70° C. Mixing can be performed for at least 1 s, at least 10 s, at least 30 s, at least 1 min, at least 10 min or at least 1 h.

In step vi) the suspension obtained in step v) is dried to obtain the inventive dry composition.

The drying may be carried out in a single step such as spray drying, or in at least two steps, e.g. by applying a first heating step to the calcium carbonate in order to reduce the associated moisture content. The residual total moisture content may be further reduced by applying a second heating step to the calcium carbonate. In case said drying is carried out by more than one drying steps, the first step may be carried out by heating in a hot current of air, while the second and further drying steps are preferably carried out by an indirect heating.

According to a preferred embodiment of the present invention, the drying in step vi) is performed at temperatures above 75° C., preferably between 75° C. and 250° C., more preferably between 100 and 230° C., more preferably between 110 and 200° C. and most preferably between 120 and 180° C.

The inventive dry composition have already been described above.

According to one embodiment of the present invention, the obtained dry composition of the present invention is in solid form, preferably in form of a particulate material. The term "particulate" in the meaning of the present application refers to materials composed of a plurality of particles. Said plurality of particles may be defined, for example, by its particle size distribution. The expression "particulate material" may comprise powders, grains, tablets, flakes or crumbles.

If the obtained dry composition is in form of a particulate material it may be further deagglomerated, for example, during a grinding step. In general, the grinding step can be carried out with any conventional grinding device, for example, under conditions such that refinement predominantly results from impacts with a secondary body, i.e. in one or more of: a mortar, a ball mill, a rod mill, a vibrating mill, a roll crusher, a centrifugal impact mill, a vertical bead mill an attrition mill, a pin mill, a hammer mill, a pulveriser, a shredder, a de-dumper, a knife cutter, or other such equipment known to the skilled man.

The inventors surprisingly found that by the above method it is possible to prepare the inventive dry composition. The method is easy to prepare, cheap and easy and safe for the operator. By the above method it is possible to prepare the inventive compositions easily and quickly.

According to a preferred embodiment of the present invention the method for preparing the inventive dry composition for chemical and physical sun protection comprises the steps of i) providing at least one aqueous solution having a pH≥10,
  ii) providing at least one lignin,
  iii) providing at least one mineral material selected from the group consisting of surface reacted calcium carbonate and/or hydromagnesite,
    wherein the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source,
  iv) mixing, in any order, the at least one aqueous solution of step i) with the lignin of step ii), to obtain a lignin solution,
  v) mixing, in any order, the lignin solution obtained in step iv) with the at least one mineral material of step iii) in an amount such that the amount of dry lignin is 0.1 wt.-% to 100 wt.-%, based on the dry weight of the at least one mineral material and
  vi) drying the suspension obtained in step v) to obtain the dry composition according to claims 1 to 12.

By the above method it is possible to prepared the inventive dry compositions with any solvent and preferably without organic solvents but merely with aqueous solutions which is especially cheap, easy to handle and environmentally friendly. Furthermore, no organic residues remain in the dry product which is especially favorable if the product is used in cosmetic formulations.

Furthermore, the inventors surprisingly found that if the pH value of the aqueous solution is ≥pH 10 a similar or the same amount of lignin can be dissolved in the aqueous solution as in the organic solvent, especially of a water-insoluble lignin selected from the group consisting of klason lignin, kraft lignin and mixtures thereof and most preferably of kraft lignin.

The obtained dry compositions of the inventive method provide sufficient or improved chemical and physical sun protection. More precisely, the inventors surprisingly found out that the dry compositions obtained by the inventive method offer two different mechanisms for UV-B and/or UV-A protection to living cells, especially to human skin by different mechanisms, namely by reflecting the UV-B and/or UV-A radiation as well as by absorbing the UV-B and/or UV-A radiation. Furthermore, the compounds used in the inventive method, namely the surface reacted calcium carbonate and/or hydromagnesite and the lignin and the solvents especially the aqueous solution having a pH≥10 are non-toxic to humans and do not provide a harmful effect on the environment. Often these compounds might be used in cosmetic applications. Furthermore, the inventors surprisingly found that the inventive method can be easily and quickly performed, is cheap and especially easy to handle.

Additionally, the inventors surprisingly found that even if the dry compositions might comprise salts such as ammonium carbonate, sodium carbonate or mixtures thereof that might have been formed during the preparation in the at least one aqueous solution having a pH≥10, the pH after reintroducing it into water does not or only slightly vary from the raw mineral materials.

The scope and interest of the invention will be better understood based on the following examples which are intended to illustrate certain embodiments of the present invention and are non-limitative.

EXPERIMENTS

Measurement Methods
  In the following, measurement methods implemented in the examples are described.
Reflectance Measurements
  Reflectance analysis was carried out with a double beam PerkinElmer Lambda 950 UV/Vis/NIR spectrophotometer equipped with a 150 mm integrating sphere with PMT and InGaAs detectors.
  The prepared dry compositions were measured by reflectance spectroscopy as shown in FIG. 1. The analysis was performed with the dry composition loaded into a sealed aluminum cup for powder samples, which was placed flush with the reflectance port of the integrating sphere. The spectrophotometer was scanned in the range 280 nm-800 nm in steps of 2 nm. A Spectralon white standard was used as 100% baseline. To get a proxy for the absorption spectrum of the dry composition, the measured reflectance spectrum was converted using the Kubelka-Munk equation $K-M=K/S=(1-R)2/2R$, where R is the reflectance and K and S are the absorption and scattering coefficient, respectively.
Particle Size Distribution
  The volume-based median particle size d50(vol) was measured by using a Malvern Mastersizer 2000 Laser Diffraction System (Malvern Instruments Plc., Great Britain). The raw data obtained by the measurement is analyzed using the Mie theory, with a particle refractive index of 1.57 and an absorption index of 0.005//using the Fraunhofer theory. The methods and instruments are known to the skilled person and are commonly used to determine particle size distributions.

BET Specific Surface Area (SSA) of Materials

The BET specific surface area was measured via the BET process according to ISO 9277:2010 using nitrogen, with the exception that prior to the measurement conditioning of the sample has been performed by heating the sample at 120° C. for a period of 60 minutes.

pH Measurement

The pH of the samples is measured by using a standard pH-meter at approximately 25° C.

Materials Used in the Examples and Sample Preparation

Mineral material: surface-reacted calcium carbonate having a volume median particle size d50 value of 5.5 μm and a specific surface area BET of 53 m²/g measured by the BET nitrogen method.

Hydromagnesite having a volume median particle size d50 value of 6 μm and a specific surface area BET of 45 m²/g measured by the BET nitrogen method Lignin: alkali lignin (also known as kraft lignin), available from Sigma-Aldrich under the number 370959-100G Organic solvent: gamma-valerolactone (GVL), available from Sigma-Aldrich under the number V403-100G.

Water: distilled water

Oil in water mixture: unguentum Alcoholum Lanae aquosum available from Caelo under the article number 3074, batch number 181705.

The following dry compositions were prepared, wherein the lignin is coated on the at least one mineral material: detailed amounts are listed in Table 1

3 g of surface-reacted calcium carbonate or hydromagnesite were dried overnight at 100° C. Up to 2.4 g of at least one lignin were solubilized in 6 g of organic solvent. Both components were maintained under mixing, at ambient temperature, using a standard magnetic stirrer, till a full solubilisation of the alkali lignin. The so-prepared lignin solution was added dropwise to the surface-reacted calcium carbonate, while mixing the surface-reacted calcium carbonate manually for an homogeneous coating. The lignin-coated surface-reacted calcium carbonate was dried overnight at 100° C. If needed, the surface-reacted calcium carbonate was deagglomerated manually using a standard lab mortar.

The following dry compositions were prepared, wherein the lignin is mixed with the at least one mineral material: detailed amounts are listed in Table 2

3 g of surface-reacted calcium carbonate or hydromagnesite were dried overnight at 100° C. Up to 2.4 g of at least one lignin were added to the surface reacted calcium carbonate or hydromagnesite. The so-prepared dry compositions were mixed manually.

TABLE 1

Lignin-coated dry compositions

| Amount of mineral material (g) | Amount of lignin (g) | Amount of lignin based on dry mineral material (wt %) | Amount of organic solvent (g) |
|---|---|---|---|
| 3.0 | 0 | 0 | 6.0 |
| 3.0 | 0.03 | 1 | 6.0 |
| 3.0 | 0.3 | 10 | 6.0 |
| 3.0 | 0.6 | 20 | 6.0 |

TABLE 1-continued

Lignin-coated dry compositions

| Amount of mineral material (g) | Amount of lignin (g) | Amount of lignin based on dry mineral material (wt %) | Amount of organic solvent (g) |
|---|---|---|---|
| 3.0 | 1.2 | 40 | 6.0 |
| 3.0 | 2.4 | 80 | 6.0 |

TABLE 2

Lignin-blended dry compositions

| Amount of mineral material (g) | Amount of lignin (g) | Amount of lignin based on dry mineral material (wt %) |
|---|---|---|
| 3.0 | 0 | 0 |
| 3.0 | 0.03 | 1 |
| 3.0 | 0.6 | 20 |
| 3.0 | 2.4 | 80 |

Reflectance Test 01

The reflectance of the above prepared dry compositions was measured and converted to an absorption spectrum using the Kubelka-Munk function. FIG. 1 shows the Kubelka-Munk function evaluated at 300 nm wavelength as a function of the lignin amount for the lignin-coated dry compositions comprising surface-reacted calcium carbonate (empty-circles) or hydromagnesite (empty squares) and for the lignin-blended dry compositions comprising surface-reacted calcium carbonate (filled circles) or hydromagnesite (filled squares).

As can be seen from FIG. 1, for all dry compositions the UV absorption increases with increasing amount of lignin. Therefore, a dry composition comprising at least one mineral material selected from the group consisting of surface reacted calcium carbonate and/or hydromagnesite, and at least one lignin in the claimed range leads to an improved UV absorption.

Additionally, it can be concluded from FIG. 1 that a lignin coating applied on the at least one mineral material selected from the group consisting of surface reacted calcium carbonate and/or hydromagnesite leads to an improved UV absorption compared to a blend of lignin with the at least one mineral material selected from the group consisting of surface reacted calcium carbonate and/or hydromagnesite.

The following solubility tests were prepared, wherein the amount of solved alkali lignin is measured in each prepared solution: detailed amounts are listed in Table 3

10 ml of each solution were measured and the pH value of each of the solutions was measured. Alkali lignin was added in portions of 0.25 g until no dissolving could be detected by the human eye. The portion of 0.25 g has been dissolved in the solution when no residues could be detected by the human eye.

Lignin: alkali lignin (also known as kraft lignin), available from Sigma-Aldrich under the number 370959-100G Solution: NaOH from Sigma Aldrich, CAS number: 228152-1 kg (≥97% ACS reagent), dissolved in water until the desired pH value Ammonium hydroxide solution, CAS number: 221228-1LA (ACS reagent 28-30%), dissolved in water until the desired pH value gamma-valerolactone (GVL), available from Sigma-Aldrich under the number V403-100G

TABLE 3

| Solution | pH | Volume (mL) | Amount of alkali lignin soluble (g) |
|---|---|---|---|
| Distilled water | 6.7 | 10 | 0 |
| NaOH solution - pH 8 | 8.3 | | 0 |
| NaOH solution - pH 12 | 12.1 | | Low solubility (ca. 0.25) |
| NaOH solution - pH 12.5 | 12.5 | | Low solubility (ca. 0.25) |
| NaOH solution - pH 13 | 13.3 | | 2.5-3 (Max) |
| GVL | 5.0 | | 3 |
| Ammonia Solution -pH 10 | 10.0 | | 0.25 |
| Ammonia Solution - pH 12 | 12.1 | | 2-2.5 (Max) |
| Commercial ammonia solution (ca. 30 wt.-%) | 12.5 | | 2-2.5 (Max) |

From table 3 it can be seen that below pH 10 it is not possible to dissolve alkali lignin in an aqueous solution, whereas it can be dissolved in an organic solvent. Between pH 10 and 14, amounts between 0.25 and 3 g of alkali lignin can be dissolved in the 10 ml aqueous solutions.

The following dry compositions were prepared, by the inventive method:

detailed amounts are listed in Table 4 and Table 5

The at least one lignin is dissolved in 15 g of the at least one organic solvent and/or at least one aqueous solution having a pH≥10 and is added stepwise to 10 g of the at least one mineral material that has been dried at 125° C. for 8 h. The suspension is dried for 8 h at 125° C. and the obtained dry composition for chemical and physical sun protection is deagglomerated with a mortar. Afterwards the specific surface area (BET) is measured of the obtained dry composition.

Lignin: alkali lignin (also known as kraft lignin), available from UPM BioPiva under the number 395

Solution: Ammonium hydroxide solution, CAS number: 221228-1LA (30 wt.-%) from Sigma Aldrich, pH value 12.5

Mineral material: surface-reacted calcium carbonate having a volume median particle size d50 value of 5.5 μm and a specific surface area BET of 42.1 $m^2$/g measured by the BET nitrogen method.

Hydromagnesite having a volume median particle size d50 value of 6 μm and a specific surface area BET of 41.7 $m^2$/g measured by the BET nitrogen method

TABLE 4

| | Surface-reacted calcium carbonate | | | |
|---|---|---|---|---|
| Sample | Amount of mineral material (g) | Amount of Lignin (g) | Amount of lignin based on dry mineral material (wt.-%) | BET ($m^2$/g) |
| 4.1 | 10.0 | 0.1 | 1 | 41.5 |
| 4.2 | 10.0 | 0.5 | 5 | 42.6 |
| 4.3 | 10.0 | 1.0 | 10 | 39.3 |
| 4.4 | 10.0 | 2.0 | 20 | 29.8 |
| 4.5 | 10.0 | 4.0 | 40 | 17.1 |

TABLE 5

| | Hydromagnesite | | | |
|---|---|---|---|---|
| Sample | Amount of mineral material (g) | Amount of Lignin (g) | Amount of lignin based on dry mineral material (wt.-%) | BET ($m^2$/g) |
| 5.1 | 10.0 | 0.1 | 1 | 45.8 |
| 5.2 | 10.0 | 0.5 | 5 | 49.0 |
| 5.3 | 10.0 | 1.0 | 10 | 47.0 |
| 5.4 | 10.0 | 2.0 | 20 | 41.0 |
| 5.5 | 10.0 | 4.0 | 40 | 32.7 |

1 g of the obtained dry compositions has been added to 19 ml of distilled water and the pH values have been measured after 3 min, 30 min, 1 h and 2 h. The values are listed in the below table 6. In addition also the pH values of raw material are measured under the same conditions.

TABLE 6

| | pH values | | | |
|---|---|---|---|---|
| Sample | 3 min | 30 min | 1 h | 2 h |
| 4.1 | 7.59 | 7.91 | 7.90 | 7.88 |
| 4.2 | 7.75 | 7.89 | 7.85 | 7.85 |
| 4.3 | 7.71 | 7.72 | 7.69 | 7.72 |
| 4.4 | 7.57 | 7.57 | 7.55 | 7.62 |
| 4.5 | 7.58 | 7.47 | 7.47 | 7.55 |
| 5.1 | 10.42 | 10.34 | 10.29 | 10.20 |
| 5.2 | 10.28 | 10.40 | 10.38 | 10.28 |
| 5.3 | 10.01 | 10.24 | 10.25 | 10.20 |
| 5.4 | 9.86 | 10.07 | 10.06 | 10.04 |
| 5.5 | 9.92 | 9.97 | 9.95 | 9.90 |
| Surface-reacted calcium carbonate | 7.50 | 7.92 | 7.97 | 7.87 |
| Hydromagnesite | 10.24 | 10.15 | 10.15 | 10.13 |

It can be seen that even if the dry compositions might comprise salts that might have been formed during the preparation in the at least one aqueous solution having a pH≥10, the pH after reintroducing it into water does not or only slightly vary from the raw mineral materials.
Reflectance Test 02

Figure 2:
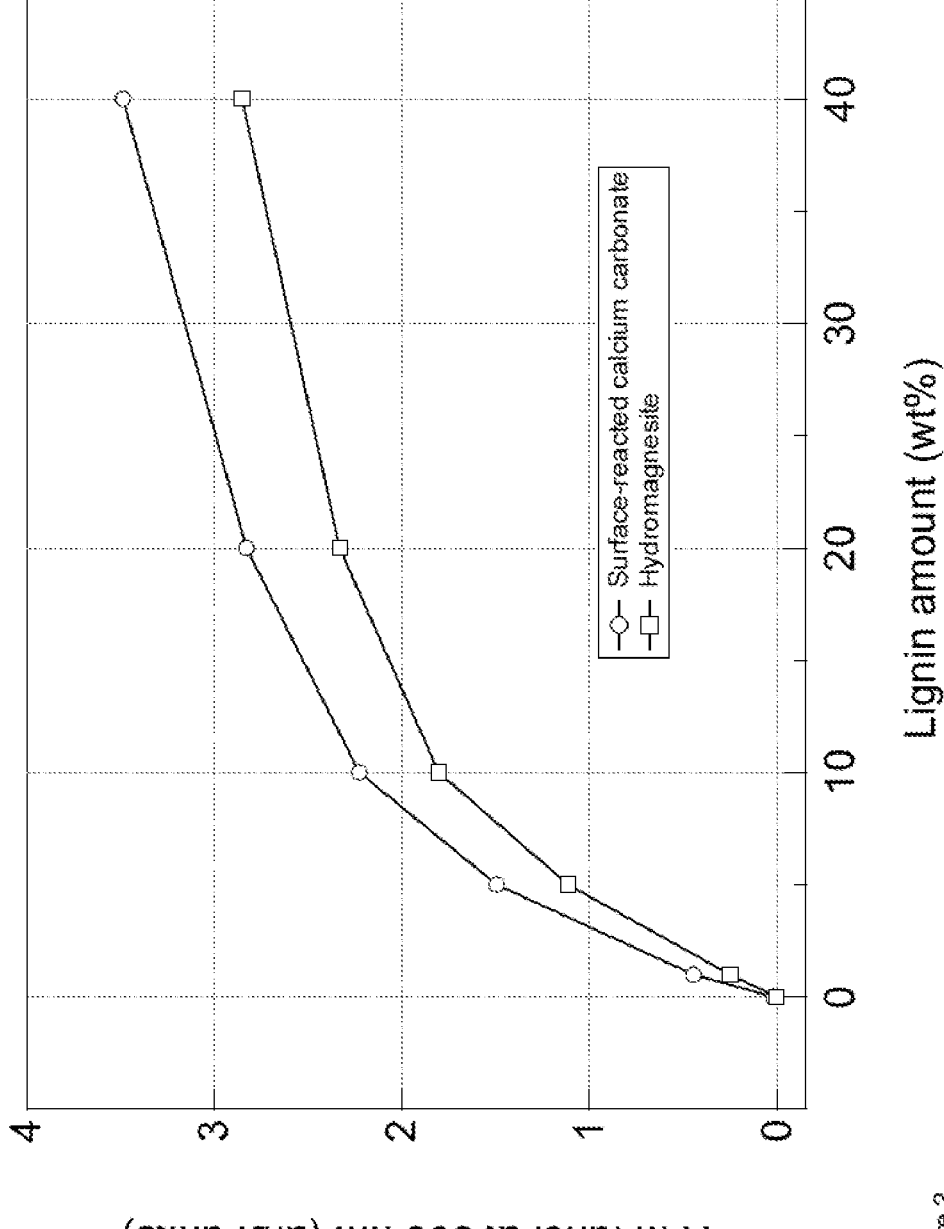
FIG. 2 shows the Kubelka-Munk function evaluated at 300 nm wavelength as a function of the lignin amount of the obtained dry compositions comprising surface-reacted calcium carbonate or hydromagnesite.

The reflectance of the above prepared dry compositions was measured and converted to an absorption spectrum using the Kubelka-Munk function. FIG. 2 shows the Kubelka-Munk function evaluated at 300 nm wavelength as a function of the lignin amount of the obtained dry compositions comprising surface-reacted calcium carbonate (black) or hydromagnesite (grey).

As can be seen from FIG. 2, for all dry compositions the UV absorption increases with increasing amount of lignin. Therefore, a dry composition comprising at least one mineral material selected from the group consisting of surface reacted calcium carbonate and/or hydromagnesite, and at least one lignin in the claimed range leads to an improved UV absorption.

Additionally, it can be concluded from FIG. 2 that a dry composition prepared by the inventive method has a good UV absorption even if it has been prepared in an aqueous solution.

The invention claimed is:
1. A dry composition for chemical and physical sun protection, the dry composition comprising
   a) at least one mineral material selected from the group consisting of surface reacted calcium carbonate and hydromagnesite, wherein the surface-reacted calcium carbonate is a reaction product of natural ground calcium carbonate or precipitated calcium carbonate with carbon dioxide and one or more $H_3O+$ ion donors, wherein the carbon dioxide is formed in situ by the $H_3O+$ ion donors treatment and/or is supplied from an external source and b) from 0.1 wt.-% to 100 wt.-% of at least one lignin, based on the dry weight of the at least one mineral material, and wherein the at least one lignin is in the form of a coating on the at least one mineral material.

2. The composition according to claim 1, wherein the at least one mineral material is surface reacted calcium carbonate and/or wherein the surface reacted calcium carbonate has a) a volume median particle size $d_{50}$ from 0.1 to 90 μm, and/or b) a volume top cut ($d_{98}$) of ≤100 μm, and/or c) a specific surface area (BET) of from 10 to 200 m$^2$/g, measured using nitrogen and the BET method according to ISO 9277:2010.

3. The composition according to claim 1, wherein the at least one mineral material is hydromagnesite and wherein the hydromagnesite has a) a volume median particle size $d_{50}$ from 1 to 75 μm, and/or b) a volume top cut ($d_{98}$) of ≤100 μm, and/or c) a specific surface area (BET) of from 25 to 200 m$^2$/g, measured using nitrogen and the BET method according to ISO 9277:2010.

4. The composition according to claim 1, wherein the at least one lignin is a water soluble or water insoluble lignin selected from the group consisting of natural lignin, klason lignin, hydrolyzed lignin, milled wood lignin, soda lignin, organosolv lignin, kraft lignin, sulphonated lignin and mixtures thereof.

5. The composition according to claim 1, wherein the at least one lignin is present in the composition in an amount from 1 to 80 wt.-%, based on the dry weight of the at least one mineral material.

6. The composition according to claim 1, wherein the composition further comprises an organic solvent in an amount of 0.1 to 200 wt.-%, based on the dry weight of the at least one mineral material and/or in an amount of 100 to 500 wt.-%, based on the dry weight of the at least one lignin.

7. The composition according to claim 6, wherein the organic solvent is selected from the group consisting of hexane, toluene, methanol, ethanol, dioxane, acetone, dimethyl sulfoxide, dimethylformamide, ethylene glycol, ethylacetate, glycerol, γ-valerolactone, polyethylene glycol, polypropylene glycol and mixtures thereof.

8. The composition according to claim 1, wherein the composition further comprises at least one inorganic UV filter selected from the group consisting of titanium dioxide, zinc oxide, iron oxide, cerium oxide, calcium-doped cerium oxide, cerium phosphate, and mixtures thereof.

9. The composition of claim 1, wherein the composition further comprises at least one organic UV filter, wherein the at least one organic UV filter is selected from the group consisting of derivatives of cinnamic acid and its salts, derivatives of salicylic acid and its salts, benzophenones, derivatives of aminobenzoic acid and its salts, dibenzoylmethanes, benzylidenecamphor derivatives, benzimidazole derivatives, diphenylacrylate derivatives, acrylamide derivatives, benzotriazole derivatives, triazine derivatives, benzalmalonate derivatives, aminobenzoate derivatives, octocrylene, and mixtures thereof.

10. The composition according to claim 1, wherein the at least one mineral material is a surface reacted calcium carbonate, and wherein surface reacted calcium carbonate is a reaction product of natural ground calcium carbonate with carbon dioxide and phosphoric acid, wherein the carbon dioxide is formed in situ by the phosphoric acid treatment.

11. The composition according to claim 1, wherein the surface reacted calcium carbonate has a volume median particle size $d_{50}$ from 1.5 to 15 μm, and the hydromagnesite has a volume median particle size $d_{50}$ from 1.2 to 50 μm.

12. The composition according to claim 1, wherein the dry composition comprises less than 5.0% water based on the total dry weight of the dry composition.

13. An emulsion for chemical and physical sun protection, the emulsion comprising a water in oil or oil in water mixture and 0.1 to 40 wt.-% of the dry composition according to claim 1, based on the weight of the water in oil or oil in water mixture.

14. A method of using the emulsion according to claim 13 for chemical and physical sun protection in a cosmetic formulation, said method comprising the step of introducing the emulsion into the cosmetic formulation, wherein the introducing step comprises mixing, dispersing and/or emulsifying said emulsion into the cosmetic formulation.

15. A method of using the emulsion according to claim 14, wherein the cosmetic formulation is a sunscreen product, facial makeup product, hair care product, hand care product, skin care product, body care product or mixtures thereof.

16. A method for preparing a dry composition for chemical and physical sun protection according to claim 1, the method comprising the steps of i) providing at least one organic solvent and/or at least one aqueous solution having a pH ≥10, ii) providing at least one lignin, iii) providing at least one mineral material selected from the group consisting of surface reacted calcium carbonate and hydromagnesite, wherein the surface-reacted calcium carbonate is a reaction product of natural ground calcium carbonate or precipitated calcium carbonate with carbon dioxide and one or more $H_3O+$ ion donors, wherein the carbon dioxide is formed in situ by the $H_3O+$ ion donors treatment and/or is supplied from an external source, iv) mixing, in any order, the at least one organic solvent and/or at least one aqueous solution of step i) with the lignin of step ii), to obtain a lignin solution, v) mixing, in any order, the lignin solution obtained in step iv) with the at least one mineral material of step iii) in an amount such that the amount of dry lignin is 0.1 wt.-% to 100 wt.-%, based on the dry weight of the at least one mineral material and vi) drying the suspension obtained in step v) to obtain the dry composition according to claim 1.

17. The method according to claim 16, where in step i) an aqueous solution having a pH≥10 is provided, and/or wherein the aqueous solution comprises caustic soda, ammonia solution, sodium hydroxide, potassium hydroxide, lye, sodium carbonate, calcium hydroxide, magnesium hydroxide and mixtures thereof.

18. The method according to claim 16, where the drying in step vi) is performed at temperatures above 75° C.

* * * * *